US008114891B2

(12) United States Patent
Pfister et al.

(10) Patent No.: US 8,114,891 B2
(45) Date of Patent: Feb. 14, 2012

(54) 4-SUBSTITUTED QUINUCLIDINE DERIVATIVES, METHODS OF PRODUCTION, PHARMACEUTICAL USES THEREOF

(75) Inventors: Jürg R. Pfister, Los Altos, CA (US); Meenakshi S. Venkatraman, Fremont, CA (US); Xiaoming Zhang, Sunnyvale, CA (US)

(73) Assignee: CoMentis, Inc., South San Francisco, CA (US)

( * ) Notice: Subject to any disclaimer, the term of this patent is extended or adjusted under 35 U.S.C. 154(b) by 693 days.

(21) Appl. No.: 12/242,389

(22) Filed: Sep. 30, 2008

(65) Prior Publication Data

US 2009/0088418 A1   Apr. 2, 2009

Related U.S. Application Data

(60) Provisional application No. 60/976,724, filed on Oct. 1, 2007.

(51) Int. Cl.
*A61K 31/439* (2006.01)
*C07D 401/12* (2006.01)

(52) U.S. Cl. ........................................ 514/305; 546/196
(58) Field of Classification Search .................... 546/196
See application file for complete search history.

(56) References Cited

U.S. PATENT DOCUMENTS

| | | | |
|---|---|---|---|
| 4,797,406 A | 1/1989 | Richardson et al. |
| 4,910,193 A | 3/1990 | Buchheit |
| 4,950,759 A | 8/1990 | van Wijngaarden et al. |
| 4,985,424 A | 1/1991 | van Wijngaarden et al. |
| 5,106,851 A | 4/1992 | Turconi et al. |
| 5,187,166 A | 2/1993 | Kikuchi et al. |
| 5,190,953 A | 3/1993 | Munson, Jr. et al. |
| 5,272,154 A | 12/1993 | Dixon et al. |
| 5,300,512 A | 4/1994 | Flynn et al. |
| 5,399,562 A | 3/1995 | Becker et al. |
| 5,512,579 A | 4/1996 | Miyazawa et al. |
| 5,543,426 A | 8/1996 | Dixon et al. |
| 5,561,149 A | 10/1996 | Azria et al. |
| 5,583,140 A | 12/1996 | Bencherif et al. |
| 5,597,919 A | 1/1997 | Dull et al. |
| 5,604,231 A | 2/1997 | Smith et al. |
| 5,658,925 A | 8/1997 | Miyazawa et al. |
| 5,672,601 A | 9/1997 | Cignarella |
| 5,677,311 A | 10/1997 | Miyazawa et al. |
| 5,712,270 A | 1/1998 | Sabb |
| 5,723,472 A | 3/1998 | Miyazawa et al. |
| 5,852,041 A | 12/1998 | Cosford et al. |
| 5,861,418 A | 1/1999 | Miyazawa et al. |
| 6,638,925 B2 | 10/2003 | Czollner et al. |
| 6,916,828 B2 | 7/2005 | Farrerons Gallemi et al. |
| 2005/0250808 A1 | 11/2005 | Xie et al. |

FOREIGN PATENT DOCUMENTS

| | | |
|---|---|---|
| EP | 0 094 742 A2 | 11/1983 |
| EP | 0 094 742 A3 | 11/1983 |
| EP | 0 094 742 B1 | 11/1983 |
| EP | 0 297 858 A2 | 1/1989 |
| EP | 0 297 858 A3 | 1/1989 |
| EP | 0 350 130 A2 | 1/1990 |
| EP | 0 350 130 A3 | 1/1990 |
| EP | 0 382 687 A2 | 8/1990 |
| EP | 0 382 687 A3 | 8/1990 |
| EP | 0 382 687 B1 | 8/1990 |
| EP | 0 491 664 A1 | 6/1992 |
| EP | 0 491 664 B1 | 6/1992 |
| GB | 2 295 387 A | 5/1996 |
| JP | 58-188885 A | 11/1983 |
| JP | 4-308950 A | 10/1992 |
| JP | 09-328469 A | 12/1997 |
| JP | 2008-525464 A | 7/2008 |
| WO | WO-93/15080 A1 | 8/1993 |
| WO | WO-94/08992 A1 | 4/1994 |
| WO | WO-96/31475 A2 | 10/1996 |
| WO | WO-96/31475 A3 | 10/1996 |
| WO | WO-96/40682 A1 | 12/1996 |
| WO | WO-97/30998 A1 | 8/1997 |
| WO | WO-97/40049 A1 | 10/1997 |
| WO | WO-99/03859 A1 | 1/1999 |
| WO | WO-99/21834 A1 | 5/1999 |
| WO | WO-99/62505 A2 | 12/1999 |
| WO | WO-99/62505 A3 | 12/1999 |
| WO | WO-01/36417 A1 | 5/2001 |
| WO | WO-02/00652 A1 | 1/2002 |
| WO | WO-02/15662 A2 | 2/2002 |
| WO | WO-02/15662 A3 | 2/2002 |
| WO | WO-02/16355 A2 | 2/2002 |
| WO | WO-02/16355 A3 | 2/2002 |
| WO | WO-02/16356 A2 | 2/2002 |
| WO | WO-02/16356 A3 | 2/2002 |
| WO | WO-02/16357 A2 | 2/2002 |
| WO | WO-02/16357 A3 | 2/2002 |

(Continued)

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/O9/24/alzheimers.drug.ap/indexhtml>.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*

(Continued)

*Primary Examiner* — Shawquia Young
(74) *Attorney, Agent, or Firm* — Morrison & Foerster LLP

(57) ABSTRACT

The present invention relates to compounds and formulations capable of affecting nicotinic acetylcholine receptors (nAChRs), for example, as modulators of specific nicotinic receptor subtypes (specifically, the alpha7 nAChR subtype). The present invention also relates to methods for treating a wide variety of conditions and disorders, particularly those associated with dysfunction of the central and autonomic nervous systems.

41 Claims, No Drawings

FOREIGN PATENT DOCUMENTS

| WO | WO-02/16358 A2 | 2/2002 |
|---|---|---|
| WO | WO-02/16358 A3 | 2/2002 |
| WO | WO-02/17358 A2 | 2/2002 |
| WO | WO-02/17358 A3 | 2/2002 |
| WO | WO-02/051841 A1 | 7/2002 |
| WO | WO-2006/069097 A2 | 6/2006 |
| WO | WO-2006/069097 A3 | 6/2006 |

OTHER PUBLICATIONS

Vippagunta, et al. Advanced Drug Delivery Reviews 48 (2001) 3-26.*

Arneric, S.P. et al. (1995). "Preclinical Pharmacology of ABT-418: A Prototypical Cholinergic Channel Activator for the Potential Treatment of Alzheimer's Disease," *CNS Drug Rev.* 1(1):1-26.

Arneric, S.P et al. (Jan. 1996). "Cholinergic Channel Modulators as a Novel Therapeutic Strategy for Alzheimer's Disease," *Exp. Opin. Invest. Drugs* 5(1):79-100.

Bannon, A.W. et al. (Jan. 2, 1998). "Broad-Spectrum, Non-Opioid Analgesic Activity by Selective Modulation of Neuronal Nicotinic Acetylcholine Receptors," *Science* 279(2):77-81.

Bencherif, M. et al. (1996). "RJR-2403: A Nicotinic Agonist with CNS Selectively I. In Vitro Characterization," *J. Pharm. and Exp. Therapeutics* 279(3):1413-1421.

Bencherif, M. et al. (Aug. 2002). "Targeting Neuronal Nicotinic Receptors: A Path to New Therapies," *Current Drug Targets: CNS and Neurological Disorders* 1(4):349-357.

Chiari, A. et al. (Nov. 1999). "Sex Differences in Cholinergic Analgesia I," *Anesthesiology* 91(5):1447-1454.

Damaj, M.I. et al. (1999). "Antinociceptive and Pharmacological Effects of Metanicotine, a Selective Nicotinic Agonist," *J. Pharmacol. Exp. Ther.* 291(1):390-398.

Dolle, F. et al. (2001, e-pub. Aug. 1, 2001). "Synthesis and Preliminary Evaluation of a Carbon-11-Labelled Agonist of the α7 Nicotinic Acetylcholine Receptor," *J. Labelled Comp. Radiopharm.* 44:785-795.

Holladay, M.W. et al. (Dec. 19, 1997). "Neuronal Nicotinic Acetylcholine Receptors as Targets for Drug Discovery," *J. Med. Chem.* 40(26):4169-4194.

International Search Report mailed Mar. 2, 2009, for PCT Application No. PCT/US2008/078320, filed Sep. 30, 2008, 1 page.

Lavand'Homme, P.M. et al. (Nov. 1999). "Sex Differences in Cholinergic Analgesia II: Differing Mechanisms in Two Models of Allodynia," *Anesthesiology* 91(5):1455-1466.

Levin, E.D. et al. (Aug. 2002). "Nicotinic Treatment for Cognitive Dysfunction," *Current Drug Targets: CNS and Neurological Disorders* 1(4):423-431.

Lippiello, P.M. et al. (1996). "RJR-2403: A Nicotinic Agonist with CNS Selectivity. II. In Vivo Characterization," *J. Pharm. and Exp. Therapeutics* 279(3):1422-1429.

Macor, J.E. et al. (2001). "The 5-HT$_3$ Antagonist Tropisetron (ICS 25-930) is a Potent and Selective α7 Nicotinic Receptor Partial Agonist," *Bioorg. Med. Chem. Lett.* 11:319-321.

Mazurov, A. et al. (2006). "Selective α7 Nicotinic Acetylcholine Receptor Ligands," *Current Medicinal Chemistry* 13:1567-1584, erratum (2007) 12(12):1593.

O'Neill, M.J. et al. (Aug. 2002). "The Role of Neuronal Nicotinic Acetylcholine Receptors in Acute and Chronic Neurodegeneration," *Current Drug Targets: CNS and Neurological Disorders* 1(4):399-411.

Stevens, K.E. et al. (1998). "Selective α$_7$-Nicotinic Agonists Normalize Inhibition of Auditory Response in DBA Mice," *Psychopharm.* 136:320-327.

Williams, M. et al. (May 1994). "Neuronal Nicotinic Acetylcholine Receptors," *Drug News & Perspectives* 7(4):205-223.

\* cited by examiner

4-SUBSTITUTED QUINUCLIDINE DERIVATIVES, METHODS OF PRODUCTION, PHARMACEUTICAL USES THEREOF

CROSS REFERENCE TO RELATED APPLICATIONS

This application claims priority benefit of U.S. Provisional Application No. 60/976,724, entitled "4-Substituted Quinuclidine Derivatives, Methods of Production, and Pharmaceutical Uses Thereof" filed Oct. 1, 2007, the content of which is hereby incorporated by reference in its entirety as if it was set forth in full below.

BACKGROUND OF THE INVENTION

Nicotine has been proposed to have a number of pharmacological effects. See, for example, Pullan et al., N. Engl. J. Med. 330, 811 (1994). Certain of those effects may be related to effects upon neurotransmitter release. See, for example, Sjak-shie et al., Brain Res. 624, 295 (1993), where neuroprotective effects of nicotine are proposed. Release of acetylcholine and dopamine by neurons, upon administration of nicotine, has been reported by Rowell et al., J. Neurochem. 43, 1593 (1984); Rapier et al., J. Neurochem. 50, 1123 (1988); Sandor et al., Brain Res. 567, 313 (1991) and Vizi, Br. J. Pharmacol. 47, 765 (1973). Release of norepinephrine by neurons, upon administration of nicotine, has been reported by Hall et al., Biochem. Pharmacol. 21, 1829 (1972). Release of serotonin by neurons, upon administration of nicotine, has been reported by Hery et al., Arch. Int. Pharmacodyn. Ther. 296, 91 (1977). Release of glutamate by neurons, upon administration of nicotine, has been reported by Toth et al., Neurochem Res. 17, 265 (1992). Confirmatory reports and additional recent studies have included the modulation, in the central nervous system (CNS), of glutamate, nitric oxide, GABA, tachykinins, cytokines, and peptides (reviewed in Brioni et al., Adv. Pharmacol. 37, 153 (1997)). In addition, nicotine reportedly potentiates the pharmacological behavior of certain formulations used for the treatment of certain disorders. See, for example, Sanberg et al., Pharmacol. Biochem. & Behavior 46, 303 (1993); Harsing et al., J. Neurochem. 59, 48 (1993) and Hughes, Proceedings from Intl. Symp. Nic. S40 (1994). Furthermore, various other beneficial pharmacological effects of nicotine have been proposed. See, for example, Decina et al., Biol. Psychiatry 28, 502 (1990); Wagner et al., Pharmacopsychiatry 21, 301 (1988); Pomerleau et al., Addictive Behaviors 9, 265 (1984); Onaivi et al., Life Sci. 54, 193 (1994); Tripathi et al., JPET 221, 91 (1982) and Hamon, Trends in Pharmacol. Res. 15, 36 (1994).

Various compounds that target nicotinic acetylcholine receptors (nAChRs) have been reported as being useful for treating a wide variety of conditions and disorders. See, for example, Williams et al., DN&P 7, 205 (1994); Arneric et al., CNS Drug Rev. 1, 1 (1995); Arneric et al., Exp. Opin. Invest. Drugs 5, 79 (1996); Bencherif et al., JPET 279, 1413 (1996); Lippiello et al., JPET 279, 1422 (1996); Damaj et al., J. Pharmacol. Exp. Ther. 291, 390 (1999); Chiari et al., Anesthesiology 91, 1447 (1999); Lavand'homme and Eisenbach, Anesthesiology 91, 1455 (1999); Holladay et al., J. Med. Chem. 40, 4169 (1997); Bannon et al., Science 279, 77 (1998); PCT WO 94/08992, PCT WO 96/31475, PCT WO 96/40682, and U.S. Pat. No. 5,583,140 to Bencherif et al., U.S. Pat. No. 5,597,919 to Dull et al., U.S. Pat. No. 5,604,231 to Smith et al., and U.S. Pat. No. 5,852,041 to Cosford et al. Nicotinic compounds are reported as being particularly useful for treating a wide variety of CNS disorders. Indeed, a wide variety of compounds have been reported to have therapeutic properties. See, for example, Bencherif and Schmitt, Current Drug Targets: CNS and Neurological Disorders 1, 349 (2002), Levin and Rezvani, Current Drug Targets: CNS and Neurological Disorders 1, 423 (2002), O'Neill et al., Current Drug Targets: CNS and Neurological Disorders 1, 399 (2002), U.S. Pat. No. 5,1871,166 to Kikuchi et al., U.S. Pat. No. 5,672,601 to Cignarella, PCT WO 99/21834, PCT WO 97/40049, UK Patent Application GB 2295387, and European Patent Application 297,858.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses, and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of choline, dopamine, norepinephrine and/or serotonin. Relatively common CNS disorders include pre-senile dementia (early-onset Alzheimer's disease), senile dementia (dementia of the Alzheimer's type), micro-infarct dementia, AIDS-related dementia, Creutzfeld-Jakob disease, Pick's disease, Parkinsonism including Parkinson's disease, Lewy body dementia, progressive supranuclear palsy, Huntington's chorea, tardive dyskinesia, hyperkinesia, mania, attention deficit disorder, anxiety, dyslexia, schizophrenia, depression, obsessive-compulsive disorders and Tourette's syndrome.

The nAChRs characteristic of the CNS have been shown to occur in several subtypes, the most common of which are the α4β2 and α7 subtypes. See, for example, Schmitt, Current Med. Chem. 7, 749 (2000). Ligands that interact with the α7 nAChR subtype have been proposed to be useful in the treatment of schizophrenia. There are a decreased number of hippocampal nAChRs in postmortem brain tissue of schizophrenic individuals. Also, there is improved psychological effect in smoking versus non-smoking schizophrenic individuals. Nicotine improves sensory gating deficits in animals and schizophrenics. Blockade of the α7 nAChR subtype induces a gating deficit similar to that seen in schizophrenia. See, for example, Leonard et al., Schizophrenia Bulletin 22, 431 (1996). Biochemical, molecular, and genetic studies of sensory processing in individuals with the P50 auditory-evoked potential gating deficit suggest that the α7 nAChR subtype may function in an inhibitory neuronal pathway. See, for example, Freedman et al., Biological Psychiatry 38, 22 (1995).

More recently, α7 nAChRs have been proposed to be mediators of angiogenesis, as described by Heeschen et al., J. Clin. Invest. 100, 527 (2002), U.S. Pat. No. 6,417,207, U.S. Pat. No. 7,045,534, WO 01/08683 and WO 01/08684. In these studies, inhibition of the α7 subtype was shown to decrease inflammatory angiogenesis. Also, α7 nAChRs have been proposed as targets for controlling neurogenesis and tumor growth (Utsugisawa et al., Molecular Brain Research 106, 88 (2002) and U.S. Patent Application 2002/0016371). Finally, the role of the α7 subtype in cognition (Levin and Rezvani, Current Drug Targets: CNS and Neurological Disorders 1, 423 (2002)), neuroprotection (O'Neill et al., Current Drug Targets: CNS and Neurological Disorders 1, 399 (2002) and Jeyarasasingam et al., Neuroscience 109, 275 (2002)), and neuropathic pain (Xiao et al., Proc. Nat. Acad. Sci. 99, 8360 (2002)) has recently been recognized.

Various compounds have been reported to interact with α7 nAChRs and have been proposed as therapies on that basis. See, for instance, WO 99/62505, WO 99/03859, WO 97/30998, WO 01/36417, WO 02/15662, WO 02/16355, WO 02/16356, WO 02/16357, WO 02/16358, WO 02/17358, Stevens et al., Psychopharm. 136, 320 (1998), Dolle et al., J. Labelled Comp. Radiopharm. 44, 785 (2001) and Macor et al., Bioorg. Med. Chem. Lett. 11, 319 (2001) and references therein. Among these compounds, a common structural theme is that of a substituted tertiary bicyclic amine (e.g., quinuclidine). Similar quinuclidine compounds have also been reported to bind to muscarinic (U.S. Pat. No. 5,712,270, WO 02/00652 and WO 02/51841) as well as serotonergic receptors (U.S. Pat. No. 5,300,512 and U.S. Pat. No. 5,399,562).

European Patent Publication No. 491664A1 discloses 3,7-disubstituted indole derivatives for treating psychiatric disorders.

PCT Publication No. WO 93/15080 discloses azabicyclo compounds as calcium channel antagonists.

European Patent Publication No. 382687A2 discloses benzofused-N-containing heterocycle derivatives as muscarinic receptor blocking agents.

European Patent Publication No. 350130A2 discloses substituted 1,7-annelated 1H-indazoles as antagonists of "neuronal" 5-HT receptors.

U.S. Pat. No. 5,399,562 discloses indolones useful as $5-HT_4$ agonists or antagonists and $5-HT_3$ antagonists.

U.S. Pat. No. 5,300,512 discloses benzimidazole compounds useful in treating $5-HT_4$ and/or $5-HT_3$ mediated conditions.

It would be desirable to provide useful methods for the prevention and treatment of nicotinic receptor-mediated conditions by administering a compound which mediates such conditions to a individual susceptible to or suffering from such a condition. It would be highly beneficial to provide individuals suffering from certain conditions (e.g., CNS diseases) with interruption of the symptoms of those conditions by the administration of a formulation containing an active ingredient having nicotinic pharmacology which has a beneficial effect (e.g., upon the functioning of the CNS), but does not provide any significant associated side effects. It would be highly desirable to provide a formulation incorporating a compound that interacts with nAChRs, such as those that have the potential to affect the functioning of the CNS. It would be highly desirable that such a compound, when employed in an amount sufficient to affect the functioning of the CNS, would not significantly affect those nAChR subtypes that have the potential to induce undesirable side effects (e.g., appreciable activity at cardiovascular and skeletal muscle receptor sites). In addition, it would be highly desirable to provide a formulation incorporating a compound which interacts with nicotinic receptors but not muscarinic receptors, as the latter are associated with side effects, such as hypersalivation, sweating, tremors, cardiovascular and gastrointestinal disturbances, related to the function of the parasympathetic nervous system (see Caulfield, Pharmacol. Ther. 58, 319 (1993) and Broadley and Kelly, Molecules 6, 142 (2001)). Furthermore, it would be highly desirable to provide formulations, which are selective for the α7 nAChR subtype, for the treatment of certain conditions (e.g., schizophrenia, cognitive disorders, neuropathic pain, diabetes, and inflammation, i.e. ulcerative colitis) and for the prevention of tissue damage and the hastening of healing (i.e. the control of angiogenesis).

All patents, patent applications, documents, and articles cited herein are herein incorporated by reference in their entirety.

BRIEF SUMMARY OF THE INVENTION

The invention embraces substituted quinuclidine derivatives as described herein, as well as formulations and kits including these compounds, which are useful for the prevention and treatment of nicotinic receptor-mediated conditions. The invention also embraces methods for the prevention and treatment of nicotinic receptor-mediated conditions, comprising administering to an individual in need thereof a therapeutically effective amount of one or more compounds as described herein.

In one aspect, the invention embraces compounds of formula (I):

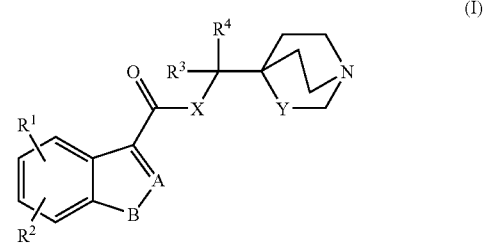

wherein

A is —N—; —CH—; or —C($C_1$-$C_6$ alkyl)-, optionally substituted with one or more groups selected from hydroxyl and halo;

B is —NH—; —N($C_1$-$C_6$ alkyl)-, optionally substituted with one or more groups selected from hydroxyl and halo; —O—; or —S—;

X is —O—; —NH—; —N($C_1$-$C_6$ alkyl)-, optionally substituted with one or more groups selected from hydroxyl and halo; —$CH_2$—; or a bond;

Y is a bond, —$CH_2$—, —$(CH_2)_2$—, —$OCH_2$—, —C(O)—, —CH($OR^7$)—, —C($OR^7$)$_2$—,

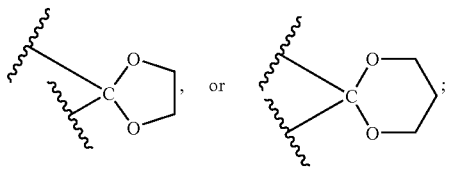

$R^7$ is independently —$C_1$-$C_6$ alkyl, optionally substituted with one or more groups selected from hydroxyl and halo;

$R^1$ and $R^2$ are each independently —H; —OH; —$C_1$-$C_6$ alkoxy, optionally substituted with one or more groups selected from hydroxyl and halo; $C_1$-$C_6$ alkyl, optionally substituted with one or more groups selected from hydroxyl and halo; —$C_1$-$C_6$ alkyl-($C_1$-$C_6$ alkoxy), optionally substituted with one or more groups selected from hydroxyl and halo; halo; —$NO_2$; —CN; —C(O)N($R_5$)$R_6$; —S(O)$_2R_5$; —S(O)$_2$N($R_5$)$R_6$; or wherein $R^1$ and $R^2$ are at adjacent carbons and together substituted with —O—$CH_2$—O— to form a ring; and $R^3$, $R^4$, $R^5$, and $R^6$ are each independently —H or —$C_1$-$C_6$ alkyl, optionally substituted with one or more groups selected from hydroxyl and halo;

or a pharmaceutically acceptable salt, isomer, mixtures of isomers, crystalline form, non-crystalline form, hydrate, or solvate thereof.

Some of these embodiments of Formula (I) have the proviso that when A is —N— or —CH—, B is —NH— or —N($C_1$-$C_3$ alkyl)-, X is —O—, Y is —$CH_2$—, $R^3$ and $R^4$ are —H, and one of $R^1$ and $R^2$ is —H, then the other of $R^1$ and $R^2$ is not -alkoxy. In certain of these embodiments, X is —O—, —$CH_2$—, or a bond.

Some of these embodiments of Formula (I) have the proviso that when A is —N— or —CH—, B is —NH— or —N($C_1$-$C_3$ alkyl)-, X is —O—, Y is —$CH_2$—, $R^3$ and $R^4$ are —H, and one of $R^1$ and $R^2$ is —H, then the other of $R^1$ and $R^2$ is not 7-alkoxy. In certain of these embodiments, X is —O—, —$CH_2$—, or a bond.

Some of these embodiments of Formula (I) have the proviso that when A is —N— or —CH—, B is —NH— or —N($C_1$-$C_3$ alkyl)-, X is —O—, Y is —$CH_2$—, $R^3$ and $R^4$ are —H, and one of $R^1$ and $R^2$ is —H, then the other of $R^1$ and $R^2$ is not 7-OH or 7-alkoxy. In certain of these embodiments, X is —O—, —$CH_2$—, or a bond.

In another aspect, the invention embraces compounds of formula (II):

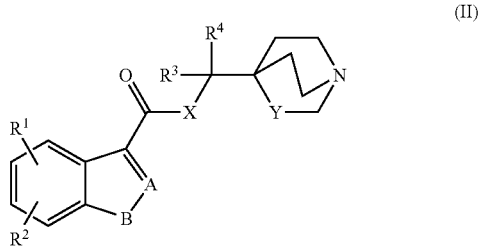

(II)

wherein

A is —N—; —CH—; or —C($C_1$-$C_6$ alkyl)-, optionally substituted with one or more groups selected from hydroxyl and halo;

B is —NH—; —N($C_1$-$C_6$ alkyl)-, optionally substituted with one or more groups selected from hydroxyl and halo; —O—; or —S—;

X is O, $CH_2$, or a bond;

Y is a bond, —$CH_2$—, —$(CH_2)_2$—, —$OCH_2$—, —C(O)—, —CH($OR^7$)—, —C($OR^7$)$_2$—,

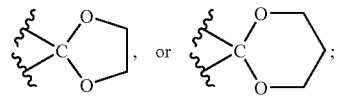

$R^7$ is —$C_1$-$C_6$ alkyl, optionally substituted with one or more groups selected from hydroxyl and halo;

$R^1$ and $R^2$ are each independently —H; —OH; —$C_1$-$C_6$ alkoxy, optionally substituted with one or more groups selected from hydroxyl and halo; —$C_1$-$C_6$ alkyl, optionally substituted with one or more groups selected from hydroxyl and halo; —$C_1$-$C_6$ alkyl-($C_1$-$C_6$ alkoxy), optionally substituted with one or more groups selected from hydroxyl and halo; halo; —$NO_2$; —CN; —C(O)N($R_5$)$R_6$; —S(O)$_2$$R_5$; —S(O)$_2$N($R_5$)$R_6$; or wherein $R^1$ and $R^2$ are at adjacent carbons and together substituted with —O—$CH_2$—O— to form a ring; and $R^3$, $R^4$, $R^5$, and $R^6$ are each independently —H or —$C_1$-$C_6$ alkyl, optionally substituted with one or more groups selected from hydroxyl and halo;

or a pharmaceutically acceptable salt, isomer, mixtures of isomers, crystalline form, non-crystalline form, hydrate, or solvate thereof.

In some embodiments, the compound is quinuclidin-4-ylmethyl 1H-indole-3-carboxylate; or a pharmaceutically acceptable salt, isomer, mixtures of isomers, crystalline form, non-crystalline form, hydrate, or solvate thereof.

In some of these embodiments of Formula I and Formula II, the compound is present in substantially pure form.

In some embodiments, the compound is any one, or any combination of the compounds of Table 1.

In another aspect, the invention embraces formulations comprising a compound described herein (e.g., a compound of Formula I, II, and/or any compound of Table 1) or a pharmaceutically acceptable salt or solvate thereof, and a carrier. In some embodiments, the carrier is a pharmaceutically acceptable carrier. In some embodiments of the formulations, the compound is present in an amount effective for treatment or prevention of a condition mediated by the α7-nicotinic acetylcholine receptor (α7-nAChR).

In another aspect, the invention embraces a method for the treatment or prevention of a condition mediated by the α7-nicotinic acetylcholine receptor (α7-nAChR), comprising the step of (a) administering to an individual in need thereof a therapeutically effective amount of any one of the compounds described herein (e.g., a compound of Formula I, II, and/or any compound of Table 1) or a pharmaceutically acceptable salt or solvate thereof.

In some embodiments of the methods, the individual is a mammal. In other embodiments, the individual is a human. In other embodiments, the individual is an adult. In other embodiments, the individual is a child. In other embodiments, the individual is an infant. In other embodiments, the individual is a pet.

In some of these embodiments, the individual has been identified as having one or more conditions mediated by α7-nAChR. In other embodiments, the individual has been identified as susceptible to one or more conditions mediated by α7-nAChR. In some of these embodiments, the condition is one or more cognitive and attention deficit symptoms associated with Alzheimer's disease, neurodegeneration associated with Alzheimer's disease, pre-senile dementia (mild cognitive impairment), or senile dementia, schizophrenia, cognitive deficits associated with schizophrenia, psychosis, cognitive deficits associated with psychosis, attention deficit disorder, attention deficit hyperactivity disorder (ADHD), mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, depression, general anxiety disorder, age-related macular degeneration, Parkinson's disease, tardive dyskinesia, Pick's disease, post traumatic stress disorder, dysregulation of food intake including bulimia and anorexia nervosa, withdrawal symptoms associated with smoking cessation and dependent drug cessation, Tourette's syndrome, glaucoma, neurodegeneration associated with glaucoma, symptoms associated with pain, pain and inflammation, TNF-α related conditions, rheumatoid arthritis, rheumatoid spondylitis, muscle degeneration, osteoporosis, osteoarthritis, psoriasis, contact dermatitis, bone resorption diseases, atherosclerosis, Paget's disease, uveititis, gouty arthritis, inflammatory bowel disease, adult respiratory distress syndrome (ARDS), Crohn's disease, rhinitis, ulcerative colitis, anaphylaxis, asthma, Reiter's syndrome, tissue rejection of a graft, ischemia reperfusion injury, stroke, multiple sclerosis, cerebral malaria, sepsis, septic shock, toxic shock syndrome, fever and myalgias due to infection, HIV-1, HIV-2, and HIV-3, cytomegalovirus (CMV), influenza, adenovirus, a herpes virus (including HSV-1, HSV-2), a herpes zoster, cancer (multiple myeloma, acute and chronic myelogenous leukemia, or cancer-associated cachexia), diabetes (pancreatic beta cell destruction, type I diabetes, or type II diabetes), wound healing (healing burns, and wounds in general including from surgery), bone fracture healing, ischemic heart disease, tinnitus, or stable angina pectoris in a mammal. In some particular embodiments, the condition is ulcerative colitis or type I diabetes. In some embodiments, the condition is ulcerative colitis. In other embodiments the condition is type I diabetes.

In some of these embodiments, the condition is an autoimmune disease. In some embodiments the autoimmune disease is Acute disseminated encephalomyelitis (ADEM), Addison's disease, Ankylosing spondylitis, Antiphospholipid antibody syndrome (APS), Aplastic anemia, Autoimmune hepatitis, Autoimmune Oophoritis, Coeliac disease, Crohn's disease, Diabetes mellitus type 1, Gestational pemphigoid, Goodpasture's syndrome, Graves' disease, Guillain-Barré syndrome (GBS), Hashimoto's disease, Idiopathic thrombocytopenic purpura, Kawasaki's Disease, Lupus erythematosus, Multiple sclerosis, Myasthenia gravis, Opsoclonus myoclonus syndrome (OMS), Optic neuritis, Ord's thyroiditis, Pemphigus, Pernicious anaemia, Primary biliary cirrhosis, Rheumatoid arthritis, Reiter's syndrome, Sjögren's syndrome, Takayasu's arteritis, Temporal arteritis, Warm autoimmune hemolytic anemia, or Wegener's granulomatosis. In some particular embodiments, the autoimmune disease is diabetes mellitus type 1 (IDDM), systemic lupus erythematosus (SLE), Sjögren's syndrome, multiple sclerosis (MS), Hashimoto's thyroiditis, Graves' disease, or rheumatoid arthritis (RA). In some embodiments the condition is rheumatoid arthritis (RA).

In some of these embodiments, the method further comprises the step of (b) administering to the individual a pharmaceutical agent, additional treatment modality, or combination thereof. In some embodiments, the pharmaceutical agent is an acetylcholinesterase inhibitor, an antipsychotic agent, or an NMDA antagonist. In some embodiments, the pharmaceutical agent is an acetylcholinesterase inhibitor. In some embodiments, the acetylcholinesterase inhibitor is selected from the group consisting of donepezil, rivastigmine, and galantamine. In some embodiments, the pharmaceutical agent, additional treatment modality, or combination thereof is an antipsychotic agent. In some embodiments, the antipsychotic agent is selected from the group consisting of aripiprazole, ziprasidone, zotepine, risperidone, quetiapine, clozapine, thiothixene, thioridazine, loxapine, haloperidol, fluphenazine and chlorpromazine. In some embodiments, the pharmaceutical agent, additional treatment modality, or combination thereof is an NMDA antagonist. In some embodiments, the NMDA antagonist is memantine.

In some of these embodiments, step (b) is performed prior to or concomitantly with step (a). In some of these embodiments, step (b) is performed after step (a).

In some of these embodiments, about 0.01 mg/kg to about 20 mg/kg of the compound (e.g., a compound of Formula I, II, and/or any compound of Table 1) or a pharmaceutically acceptable salt or solvate thereof is administered to the individual. In some embodiments, about 0.1 mg/kg to about 5 mg/kg of the compound is administered to the individual.

In some of these embodiments, the compound or formulation thereof is administered to the individual two or more times.

In certain embodiments, the invention embraces a kit for the treatment or prevention in an individual of a condition mediated by the α7-nicotinic acetylcholine receptor (α7-nAChR), comprising: (a) at least one of the compounds described herein (e.g., a compound of Formula I, II, and/or any compound of Table 1) or a pharmaceutically acceptable salt or solvate thereof; and (b) packaging.

In certain embodiments, the invention embraces a kit for the treatment or prevention in an individual of a condition mediated by the α7-nicotinic acetylcholine receptor (α7-nAChR), comprising: (a) a formulation described herein; and (b) packaging.

In another aspect of the invention is provided the use of the compounds and formulations as described herein in the treatment or prevention in an individual of a condition mediated by the α7-nAChR as described herein. Further, the formulations thereof, as described herein, are also intended for use in the treatment or prevention in an individual of a condition mediated by the α7-nAChR and, in accordance with the methods, as described herein, unless clearly dictated otherwise by context or specifically noted.

In a further aspect of the invention is provided the use of the compounds and formulations as described herein in the manufacture of a medicament, and particularly, in the manufacture of a medicament for use in the treatment or prevention in an individual of a condition mediated by the α7-nAChR as described herein. Further, the formulations thereof, as described herein, are also intended for use in the manufacture of a medicament for use in the treatment or prevention in an individual of a condition mediated by the α7-nAChR and, in accordance with the methods, as described herein, unless clearly dictated otherwise by context or specifically noted.

Unless otherwise noted, the compounds and formulations as described herein are intended for use in the methods of treatment or prevention in an individual of a condition mediated by the α7-nAChR as described herein and may be incorporated in the kits described herein.

DETAILED DESCRIPTION OF THE INVENTION

Provided herein are compounds and formulations that may be useful in the prevention and treatment of α7-nicotinic acetylcholine receptor (α7-nAChR) mediated conditions including methods for administering a therapeutically effective amount of a compound or formulation that mediates such conditions to an individual susceptible to or suffering from such a condition. Individuals suffering from certain conditions (e.g., CNS diseases) may be provided with interruption or amelioration of the symptoms of those conditions, by the administration of a formulation containing an active ingredient (e.g., having nicotinic pharmacology) which has a beneficial effect (e.g., upon the functioning of the CNS), but does not provide any significant associated side effects. The compounds of the invention may have the advantageous property such that administration of the compound in an amount sufficient to affect the functioning of the CNS would not significantly affect those nAChR subtypes that have the potential to induce undesirable side effects (e.g., appreciable activity at cardiovascular and skeletal muscle receptor sites). These compounds may further interact with nicotinic receptors but not muscarinic receptors, as the latter are associated with side effects, such as hypersalivation, sweating, tremors, cardiovascular and gastrointestinal disturbances, related to the function of the parasympathetic nervous system. These compounds may further be selective for the α7 nAChR subtype, for the treatment of certain conditions (e.g., schizophrenia, cognitive disorders, neuropathic pain, diabetes, and inflammation, e.g., ulcerative colitis) and for the prevention of tissue damage and the hastening of healing (e.g., the control of angiogenesis).

The term "alkyl" refers to saturated aliphatic and alicyclic groups including straight-chain, branched-chain, cyclic groups, and combinations thereof, having the number of carbon atoms specified, or if no number is specified, having up to 12 carbon atoms. "Straight-chain alkyl" or "linear alkyl" groups refers to alkyl groups that are neither cyclic nor branched, commonly designated as "n-alkyl" groups. Examples of alkyl groups include, but are not limited to, groups such as methyl, ethyl, n-propyl, isopropyl, butyl, n-butyl, isobutyl, sec-butyl, t-butyl, pentyl, n-pentyl, hexyl, heptyl, octyl, nonyl, decyl, undecyl, dodecyl, neopentyl, cyclopropyl, cyclobutyl, cyclopentyl, cyclohexyl, and adamantyl. Cycloalkyl groups can consist of one ring, including, but not limited to, groups such as cycloheptyl, or multiple fused rings, including, but not limited to, groups such as adamantyl or norbornyl.

The term "alkoxy" as used herein refers to a hydrocarbon group (e.g., alkyl, alkenyl, or alkynyl) linked to an oxygen atom and having the number of carbon atoms specified, or if no number is specified, having up to 12 carbon atoms. Examples of alkoxy groups include, but are not limited to, groups such as methoxy, ethoxy, propyloxy (propoxy) (either n-propoxy or i-propoxy), and butoxy (either n-butoxy, i-butoxy, sec-butoxy, or tert-butoxy). In some embodiments, the alkoxy substituent is methoxy. In some embodiments, the alkoxy substituent is cyclopropoxy.

The term "substituted" refers to the replacement of one or more hydrogen atoms of a moiety with a monovalent or divalent radical. "Optionally substituted" indicates that the moiety may be substituted or unsubstituted. A moiety lacking the terms "optionally substituted" and "substituted" is intended an unsubstituted moiety (e.g., "phenyl" is intended an unsubstituted phenyl unless indicated as a substituted phenyl or an optionally substituted phenyl).

The terms "halo" and "halogen" as used herein refer to the Group VIIa elements (Group 17 elements in the 1990 IUPAC Periodic Table, IUPAC Nomenclature of Inorganic Chemistry, Recommendations 1990) and include Cl, Br, F and I substituents. In some embodiments, halogen substituents are Cl and F.

As used herein, "isomer" includes all stereoisomers of the compounds referred to in the formulas herein, including enantiomers, diastereomers, as well as all conformers, rotomers, and tautomers. The invention includes all enantiomers of any chiral compound disclosed, in either substantially pure levorotatory or dextrorotatory form, or in a racemic mixture, or in any ratio of enantiomers. For compounds disclosed as an (R)-enantiomer, the invention also includes the (S)-enantiomer; for compounds disclosed as the (S)-enantiomer, the invention also includes the (R)-enantiomer. The invention includes any diastereomers of the compounds referred to in the above formulas in diastereomerically pure form and in the form of mixtures in all ratios.

Unless stereochemistry is explicitly indicated in a chemical structure or chemical name, the chemical structure or chemical name is intended to embrace all possible stereoisomers, conformers, rotomers, and tautomers of the compound depicted. For example, a compound containing a chiral carbon atom (such as the carbon with $R^4$ and $R^5$) is intended to embrace both the (R) enantiomer and the (S) enantiomer. Similarly, a compound where Y is —$CH(OR^7)$— is intended to embrace both the (R) enantiomer and the (S) enantiomer. A compound containing a stereocenter with substituents $R^4$ and $R^5$ and a stereocenter on the quinuclidine (such as Y=—CH($OR^7$)—) is intended to embrace all enantiomers and diastereomers (including (R,R), (S,S), (R,S), and (R,S) isomers).

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) Protective Groups in Organic Synthesis, 3rd Ed. (John Wiley & Sons, Inc., New York), the content of which is incorporated by reference herein. Amino protecting groups include, but are not limited to, mesitylenesulfonyl (Mts), benzyloxycarbonyl (CBz or Z), t-butyloxycarbonyl (Boc), t-butyldimethylsilyl (TBS or TBDMS), 9-fluorenylmethyloxycarbonyl (Fmoc), tosyl, benzenesulfonyl, 2-pyridyl sulfonyl, or suitable photolabile protecting groups such as 6-nitroveratryloxy carbonyl (Nvoc), nitropiperonyl, pyrenylmethoxycarbonyl, nitrobenzyl, α-,α-dimethyl-dimethoxybenzyloxycarbonyl (DDZ), 5-bromo-7-nitroindolinyl, and the like. Hydroxyl protecting groups include, but are not limited to, Fmoc, TBS, photolabile protecting groups (such as nitroveratryl oxymethyl ether (Nvom)), Mom (methoxy methyl ether), and Mem (methoxy ethoxy methyl ether), NPEOC (4-nitrophenethyloxycarbonyl) and NPEOM (4-nitrophenethyloxymethyloxycarbonyl).

Certain compounds of the present invention can exist in unsolvated forms as well as solvated forms (i.e., "solvates"). Compounds of the invention may also include hydrated forms (i.e., "hydrates"). A hydrate form may also be considered a solvate form. In general, the solvated and hydrated forms are equivalent to unsolvated forms and are encompassed within the scope of the present invention. The invention also includes all polymorphs, including crystalline and non-crystalline forms. In general, all physical forms are equivalent for the uses contemplated by the present invention and are intended to be within the scope of the present invention.

The invention includes all salts of the compounds described herein, as well as methods of using such salts of the compounds. The invention also includes all non-salt forms of any salt of a compound named herein, as well as other salts of any salt of a compound named herein. In one embodiment, the salts of the compounds comprise pharmaceutically acceptable salts. "Pharmaceutically acceptable salts" are those salts which retain the biological activity of the free compounds and which can be administered as drugs or pharmaceuticals to humans and/or animals. The desired salt of a basic functional group of a compound (such as a quinuclidine nitrogen or a heterocyclic nitrogen) may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. The desired salt of an acidic functional group of a compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N'-dibenzylethylenediamine, and triethylamine salts.

Metabolites and prodrugs of the compounds referred to in the formulas herein (e.g., a compound of Formula I, II, and/or any compound of Table 1) are also embraced by the invention. However, metabolites of substances which occur naturally in individuals are excluded from the claimed compounds of the invention.

In all uses of the compounds of the formulas disclosed herein (e.g., a compound of Formula I, II, and/or any compound of Table 1), the invention also includes use of any or all of the stereochemical, enantiomeric, diastereomeric, conformeric, rotomeric, tautomeric, solvate, hydrate, polymorphic, crystalline form, non-crystalline form, salt, pharmaceutically acceptable salt, metabolite and prodrug variations of the compounds as described.

A substantially pure compound means that the compound is present with no more than 15% or no more than 10% or no more than 5% or no more than 3% or no more than 1% of the total amount of compound as impurity and/or in a different form. For instance, substantially pure S,S compound means that no more than 15% or no more than 10% or no more than 5% or no more than 3% or no more than 1% of the total R,R; S,R; and R,S form is present.

As used herein, "therapeutically effective amount" indicates an amount that results in a desired pharmacological and/or physiological effect for the condition. The effect may be prophylactic in terms of completely or partially preventing a condition or symptom thereof and/or may be therapeutic in terms of a partial or complete cure for the condition and/or adverse effect attributable to the condition. For example, a partial or complete cure of schizophrenia may be indicated by a clinical improvement of schizophrenia, such as improvement in cognitive impairment.

As used herein, the term "pharmaceutically acceptable carrier," and cognates thereof, refers to adjuvants, binders, diluents, etc. known to the skilled artisan that are suitable for administration to an individual (e.g., a mammal or non-mammal). Combinations of two or more carriers are also contemplated in the present invention. The pharmaceutically acceptable carrier(s) and any additional components, as described herein, should be compatible for use in the intended route of administration (e.g., oral, parenteral) for a particular dosage form. Such suitability will be easily recognized by the skilled artisan, particularly in view of the teaching provided herein.

As used herein, the term "pharmaceutical agent" or "additional pharmaceutical agent," and cognates of these terms, are intended to refer to active agents other than the claimed compounds of the invention, for example, drugs, which are administered to elicit a therapeutic effect. The pharmaceutical agent(s) may be directed to a therapeutic effect related to the condition that a claimed compound is intended to treat or prevent (e.g., conditions mediated by alpha7 neuronal nicotinic receptors, including, but not limited to those conditions described herein (e.g., Alzheimer's disease, Parkinson's disease, Huntington's disease, schizophrenia, ADHD, inflammatory bowel disease, etc.)), or, the pharmaceutical agent may be intended to treat or prevent a symptom of the underlying condition (e.g., promote cognition enhancement, attention, working memory, episodic secondary memory, memory recall, sensory gating, reaction time, immediate and delayed word recall, visual tracking, and word recognition) or to further reduce the appearance or severity of side effects of administering a claimed compound.

When used with respect to methods of treatment/prevention and the use of the compounds and formulations thereof described herein, an individual "in need thereof" may be an individual who has been diagnosed with or previously treated for the condition to be treated. With respect to prevention, the individual in need thereof may also be an individual who is at risk for a condition (e.g., a family history of the condition, life-style factors indicative of risk for the condition, etc.).

In some embodiments, the individual is a mammal, including, but not limited to, bovine, horse, feline, rabbit, canine, rodent, or primate. In some embodiments, the mammal is a primate. In some embodiments, the primate is a human. In some embodiments, the individual is human, including adults, children and premature infants. In some embodiments, the individual is a non-mammal. In some variations, the primate is a non-human primate such as chimpanzees and other apes and monkey species. In some embodiments, the mammal is a farm animal such as cattle, horses, sheep, goats, and swine; pets such as rabbits, dogs, and cats; laboratory animals including rodents, such as rats, mice, and guinea pigs; and the like. Examples of non-mammals include, but are not limited to, birds, and the like. The term "individual" does not denote a particular age or sex.

In some variations, the individual has been identified as having one or more of the conditions described herein. Identification of the conditions as described herein by a skilled physician is routine in the art and may also be suspected by the individual or others, for example, due to loss of memory in the case of Alzheimer's, exhibiting the symptoms of schizophrenia, etc.

In some embodiments, the individual has been identified as susceptible to one or more of the conditions as described herein. The susceptibility of an individual may be based on any one or more of a number of risk factors and/or diagnostic approaches appreciated by the skilled artisan, including, but not limited to, genetic profiling, family history, medical history (e.g., appearance of related conditions), lifestyle or habits.

As used herein and in the appended claims, the singular forms "a", "an" and "the" include plural forms, unless the context clearly dictates otherwise.

Reference to "about" a value or parameter herein includes (and describes) variations that are directed to that value or parameter per se. For example, a description referring to "about X" includes the description of "X".

Unless defined otherwise or clearly indicated by context, all technical and scientific terms used herein have the same meaning as commonly understood by one of ordinary skill in the art to which this invention belongs.

Quinuclidine Compounds

The nomenclature of certain quinuclidine compounds described herein may be determined using ChemDraw Ultra 10. The skilled artisan will recognize that a compound may be given more than one chemical name, and different chemical names may be used to describe the same compound (e.g., using more than one nomenclature convention).

In certain embodiments, the invention embraces compounds of Formula (I):

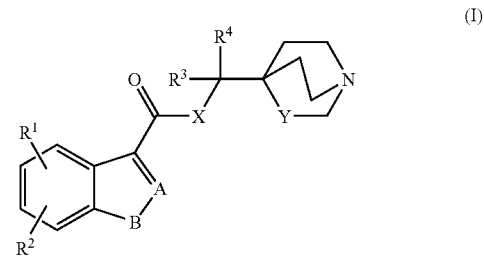

(I)

wherein

A is —N—; —CH—; or —C(C$_1$-C$_6$ alkyl)-, optionally substituted with one or more groups selected from hydroxyl and halo;

B is —NH—; —N(C$_1$-C$_6$ alkyl)-, optionally substituted with one or more groups selected from hydroxyl and halo; —O—; or —S—;

X is —O—; —NH—; —N(C$_1$-C$_6$ alkyl)-, optionally substituted with one or more groups selected from hydroxyl and halo; —CH$_2$—; or a bond;

Y is a bond, —CH$_2$—, —(CH$_2$)$_2$—, —OCH$_2$—, —C(O)—, —CH(OR$^7$)—, —C(OR$^7$)$_2$—,

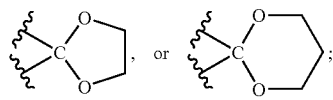

R$^7$ is independently —C$_1$-C$_6$ alkyl, optionally substituted with one or more groups selected from hydroxyl and halo;

R$^1$ and R$^2$ are each independently —H; —OH; —C$_1$-C$_6$ alkoxy, optionally substituted with one or more groups selected from hydroxyl and halo; C$_1$-C$_6$ alkyl, optionally substituted with one or more groups selected from hydroxyl and halo; —C$_1$-C$_6$ alkyl-(C$_1$-C$_6$ alkoxy), optionally substituted with one or more groups selected from hydroxyl and halo; halo; —NO$_2$; —CN; —C(O)N(R$_5$)R$_6$; —S(O)$_2$R$_5$; —S(O)$_2$N(R$_5$)R$_6$; or wherein R$^1$ and R$^2$ are at adjacent carbons and together substituted with —O—CH$_2$—O— to form a ring; and R$^3$, R$^4$, R$^5$, and R$^6$ are each independently —H or —C$_1$-C$_6$ alkyl, optionally substituted with one or more groups selected from hydroxyl and halo;

or a pharmaceutically acceptable salt, isomer, mixtures of isomers, crystalline form, non-crystalline form, hydrate, or solvate thereof.

In some embodiments of Formula (I),

A is —N—; —CH—; or —C(C$_1$-C$_3$ alkyl)-;

B is —NH—; —N(C$_1$-C$_3$ alkyl)-; —O—; or —S—;

X is —O—; —NH—; —N(C$_1$-C$_3$ alkyl)-; —CH$_2$—; or a bond;

Y is a bond, —CH$_2$—, —(CH$_2$)$_2$—, —OCH$_2$—, —C(O)—, —CH(OR$^7$)—, —C(OR$^7$)$_2$—,

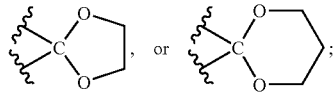

R$^7$ is —C$_1$-C$_3$ alkyl;

R$^1$ and R$^2$ are each independently —H; —OH; —C$_1$-C$_6$ alkoxy, optionally substituted with hydroxyl; C$_1$-C$_6$ alkyl, optionally substituted with hydroxyl; halo; —NO$_2$; —CN; —C(O)N(R$_5$)R$_6$; —S(O)$_2$R$_5$; —S(O)$_2$N(R$_5$)R$_6$; —OCF$_3$; —OCHF$_2$, —OCF$_3$; or wherein R$^1$ and R$^2$ are at adjacent carbons and together substituted with —O—CH$_2$—O— to form a ring; and where R$^3$, R$^4$, R$^5$, and R$^6$ are each independently —H or —C$_1$-C$_3$ alkyl;

or a pharmaceutically acceptable salt, isomer, mixtures of isomers, crystalline form, non-crystalline form, hydrate, or solvate thereof.

In some embodiments of Formula (I), A is —N—; —CH—; or —C(C$_1$-C$_3$ alkyl)-. In other embodiments, —N—, —CH—, or —C(CH$_3$)—. In other embodiments, A is —N—. In other embodiments, A is —CH—. In other embodiments, A is —C(C$_1$-C$_6$ alkyl)-. In other embodiments, A is —C(C$_1$-C$_3$ alkyl)-. In other embodiments, A is —C(CH$_3$)—. In other embodiments, A is —C(CH$_2$CH$_3$)—. In other embodiments, A is —C(CH$_2$CH$_2$CH$_3$)—. In other embodiments, A is —C(CH(CH$_3$)$_2$)—. In any of these embodiments, the alkyl (e.g., of —C(C$_1$-C$_6$ alkyl)- or —C(C$_1$-C$_3$ alkyl)-) may be substituted, for example, substituted with one or more groups selected from hydroxyl and halo.

In some of these embodiments of Formula (I), B is —NH—; —N(C$_1$-C$_3$ alkyl)-; —O—; or —S—. In some embodiments, B is —NH—, —O—, or —S—. In other embodiments, B is —NH— or —S—. In other embodiments, B is —NH— or —O—. In other embodiments, B is —O— or —S—. In other embodiments, B is —NH—. In other embodiments, B is —S—. In other embodiments, B is —O—. In other embodiments, B is —N(C$_1$-C$_6$ alkyl)-. In other embodiments, B is —N(C$_1$-C$_3$ alkyl)-. In other embodiments, B is —N(CH$_3$)—. In other embodiments, B is —N(CH$_2$CH$_3$)—. In other embodiments, B is —N(CH$_2$CH$_2$CH$_3$)—. In other embodiments, B is —C(CH(CH$_3$)$_2$)—. In other embodiments, B is —O—. In any of these embodiments, the alkyl (e.g., —N(C$_1$-C$_6$ alkyl)- or —N(C$_1$-C$_3$ alkyl)-) may be substituted, for example, substituted with one or more groups selected from hydroxyl and halo.

In some of these embodiments of Formula (I), X is —O—; —NH—; —N(C$_1$-C$_3$ alkyl)-. In some embodiments, X is —O—, —CH$_2$—, or a bond. In other embodiments, X is —O— or —NH—. In other embodiments, X is —O—. In other embodiments, X is —NH—. In other embodiments, X is —CH$_2$—. In other embodiments, X is a bond. In other embodiments, X is —N(C$_1$-C$_6$ alkyl)-. In other embodiments, X is —N(C$_1$-C$_3$ alkyl)-. In other embodiments, X is —N(CH$_3$)—. In other embodiments, X is —N(CH$_2$CH$_3$)—. In other embodiments, X is —N(CH$_2$CH$_2$CH$_3$)—. In other embodiments, X is —N(CH(CH$_3$)$_2$)—. In any of these embodiments, the alkyl (e.g., —N(C$_1$-C$_6$ alkyl)- or —N(C$_1$-C$_3$ alkyl)-) may be substituted, for example, substituted with one or more groups selected from hydroxyl and halo.

In some embodiments of Formula (I), Y is —CH$_2$—, —(CH$_2$)$_2$—, —OCH$_2$—, —C(O)—, or a bond. In other embodiments, Y is —CH$_2$—, —(CH$_2$)$_2$—, —C(O)—, or a bond. In other embodiments, Y is —CH$_2$—, —(CH$_2$)$_2$—, or a bond. In other embodiments, Y is —CH$_2$—, —C(O)—, or a bond. In other embodiments, Y is —CH$_2$— or —C(O)—. In other embodiments, Y is —CH$_2$—. In other embodiments, Y is —(CH$_2$)$_2$—. In other embodiments, Y is —OCH$_2$—. In other embodiments, Y is a bond. In other embodiments, Y is —C(O)—. In other embodiments, Y is —CH(OR$^7$)—. In other embodiments, Y is —CH(OCH$_3$)—. In other embodiments, Y is —CH(OCH$_2$CH$_3$)—. In other embodiments, Y is —CH(OCH$_2$CH$_2$CH$_3$)—. In other embodiments, Y is —CH(OCH(CH$_3$)$_2$)—. In other embodiments, Y is —C(OR$^7$)$_2$—. In other embodiments, Y is

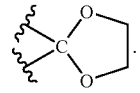

In other embodiments, Y is

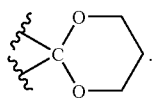

In some embodiments, each $R^7$ is independently —$C_1$-$C_6$ alkyl (or —$C_1$-$C_3$ alkyl), optionally substituted, for example, optionally substituted with one or more groups selected from hydroxyl and halo.

In some of these embodiments of Formula (I), $R^1$ and $R^2$ are each independently —H; —OH; —$C_1$-$C_6$ alkyl (or —$C_1$-$C_3$ alkyl) (or —$C_1$-$C_3$ alkyl-($C_1$-$C_3$ alkoxy)), optionally substituted with hydroxyl or halo; —$C_1$-$C_6$ alkyl-($C_1$-$C_6$ alkoxy), optionally substituted with one or more groups selected from hydroxyl and halo; halo; —$NO_2$; —CN; —C(O)N($R_5$)$R_6$; —S(O)$_2$$R_5$; —S(O)$_2$N($R_5$)$R_6$; —$CF_3$; —$OCHF_2$; —$OCF_3$; or wherein $R^1$ and $R^2$ are together substituted with —O—$CH_2$—O— to form a ring. In other embodiments, $R^1$ and $R^2$ are each independently —H; —$C_1$-$C_6$ alkyl (or —$C_1$-$C_3$ alkyl), optionally substituted with hydroxyl or halo; halo; —$NO_2$; —CN; —C(O)N($R_5$)$R_6$; —S(O)$_2$$R_5$; —S(O)$_2$N($R_5$)$R_6$; —$CF_3$; —$OCHF_2$; —$OCF_3$; or wherein $R^1$ and $R^2$ are together substituted with —O—$CH_2$—O— to form a ring. In other embodiments, $R^1$ and $R^2$ are each independently —H, —OH, —$C_1$-$C_6$ alkyl (or —$C_1$-$C_3$ alkyl), halo, —$NO_2$, —CN, —$CONH_2$, or —$SO_2CH_3$. In other embodiments, $R^1$ and $R^2$ are each independently —H, —$C_1$-$C_6$ alkyl (or —$C_1$-$C_3$ alkyl), halo, —$NO_2$, —CN, —$CONH_2$, or —$SO_2CH_3$. In other embodiments, $R^1$ and $R^2$ are each independently —H, —$C_1$-$C_3$ alkoxy, —Cl, —F, —CN, or —$CONH_2$. In other embodiments, $R^1$ and $R^2$ are each independently —H, —$OCH_3$, —Cl, —F, —CN, or —$CONH_2$. In other embodiments, $R^1$ and $R^2$ is not —H. In other embodiments, $R^1$ and $R^2$ is —H. In other embodiments, $R^1$ or $R^2$ is —H, and the other is —$OCH_3$, —Cl, —F, —CN, or —$CONH_2$. In other embodiments, $R^1$ or $R^2$ is —H, and the other is —CN or —$CONH_2$. In other embodiments, $R^1$ or $R^2$ is —H, and the other is —OH. In other embodiments, $R^1$ or $R^2$ is —H, and the other is —$C_1$-$C_6$ alkyl-($C_1$-$C_6$ alkoxy) (or —$C_1$-$C_3$ alkyl-($C_1$-$C_3$ alkoxy)) optionally substituted with one or more groups selected from hydroxyl and halo. In other embodiments, $R^1$ or $R^2$ is —H, and the other is —$C_1$-$C_6$ alkyl (or —$C_1$-$C_3$ alkyl), optionally substituted with hydroxyl or halo. In other embodiments, $R^1$ or $R^2$ is —H, and the other is —$C_1$-$C_6$ alkoxy (or —$C_1$-$C_3$ alkyl), optionally substituted with hydroxyl or halo. In other embodiments, $R^1$ or $R^2$ is —H, and the other is halo. In other embodiments, $R^1$ or $R^2$ is —H, and the other is —$NO_2$. In other embodiments, $R^1$ or $R^2$ is —H, and the other is —CN. In other embodiments, $R^1$ or $R^2$ is —H, and the other is —C(O)N($R_5$)$R_6$. In other embodiments, $R^1$ or $R^2$ is —H, and the other is —S(O)$_2$$R_5$. In other embodiments, $R^1$ or $R^2$ is —H, and the other is —S(O)$_2$N($R_5$)$R_6$. In other embodiments, $R^1$ or $R^2$ is —H, and the other is —$CF_3$. In other embodiments, $R^1$ or $R^2$ is —H, and the other is —$OCHF_2$. In other embodiments, $R^1$ or $R^2$ is —H, and the other is —$OCF_3$. In other embodiments, $R^1$ or $R^2$ is —H, and the other is —$OCH_2F$. In other embodiments, $R^1$ or $R^2$ is located at the 5-position and is not —H. In other embodiments, $R^1$ or $R^2$ is 5-$OCH_3$, 5-Cl, 5-F, 5-CN, or 5-$CONH_2$. In other embodiments, $R^1$ and $R^2$ are not —H. In other embodiments, $R^1$ and $R^2$ are —$C_1$-$C_6$ alkyl (or —$C_1$-$C_3$ alkyl). In other embodiments, $R^1$ and $R^2$ are —$C_1$-$C_6$ alkoxy (or —$C_1$-$C_3$ alkoxy). In other embodiments, $R^1$ and $R^2$ are —$OCH_3$. In other embodiments, $R^1$ and $R^2$ are halo. In other embodiments, $R^1$ and $R^2$ are at adjacent carbons and together substituted with —O—$CH_2$—O— to form a ring.

In some of these embodiments of Formula (I), both $R^5$ and $R^6$ are —H. In other embodiments, both $R^5$ and $R^6$ are —$C_1$-$C_6$ alkyl (or —$C_1$-$C_3$ alkyl). In other embodiments, both $R^5$ and $R^6$ are —$CH_3$. In other embodiments, both $R^5$ and $R^6$ are —$CH_2CH_3$. In other embodiments, both $R^5$ and $R^6$ are —$CH_2CH_2CH_3$. In other embodiments, both $R^5$ and $R^6$ are —$CH(CH_3)_2$. In other embodiments, one of $R^5$ or $R^6$ is —H, and the other is —$C_1$-$C_3$ alkyl. In other embodiments, one of $R^5$ or $R^6$ is —H, and the other is —$CH_3$. In other embodiments, one of $R^5$ or $R^6$ is —H, and the other is —$CH_2CH_3$. In other embodiments, one of $R^5$ or $R^6$ is —H, and the other is —$CH_2CH_2CH_3$. In other embodiments, one of $R^5$ or $R^6$ is —H, and the other is —$CH(CH_3)_2$. In other embodiments, at least one of $R^3$ and $R^4$ is —H. In other embodiments, at least one of $R^3$ and $R^4$ is not —H. In other embodiments, both $R^3$ and $R^4$ are —H. In other embodiments, both $R^3$ and $R^4$ are —$C_1$-$C_6$ alkyl (or —$C_1$-$C_3$ alkyl). In other embodiments, one of $R^3$ or $R^4$ is —H, and the other is —$CH_3$. In other embodiments, one of $R^3$ or $R^4$ is —H, and the other is —$CH_2CH_3$. In other embodiments, $R^3$ or $R^4$ is —H, and the other is —$CH_2CH_2CH_3$. In other embodiments, $R^3$ or $R^4$ is —H, and the other is —$CH(CH_3)_2$. In any of these embodiments, the alkyl (e.g., —$C_1$-$C_6$ alkyl or —$C_1$-$C_3$ alkyl) may be substituted, for example, substituted with one or more groups selected from hydroxyl and halo.

Some of these embodiments of Formula (I) have the proviso that when A is —N— or —CH—, B is —NH— or —N($C_1$-$C_3$ alkyl)-, X is —O—, Y is —$CH_2$—, $R^3$ and $R^4$ are —H, and one of $R^1$ and $R^2$ is —H, then the other of $R^1$ and $R^2$ is not alkoxy. In certain of these embodiments, X is —O—, —$CH_2$—, or a bond.

Some of these embodiments of Formula (I) have the proviso that when A is —N— or —CH—, B is —NH— or —N($C_1$-$C_3$ alkyl)-, X is —O—, Y is —$CH_2$—, $R^3$ and $R^4$ are —H, and one of $R^1$ and $R^2$ is —H, then the other of $R^1$ and $R^2$ is not 7-alkoxy. In certain of these embodiments, X is —O—, —$CH_2$—, or a bond.

Some of these embodiments of Formula (I) have the proviso that when A is —N— or —CH—, B is —NH— or —N($C_1$-$C_3$ alkyl)-, X is —O—, Y is —$CH_2$—, $R^3$ and $R^4$ are —H, and one of $R^1$ and $R^2$ is —H, then the other of $R^1$ and $R^2$ is not 7-OH or 7-alkoxy. In certain of these embodiments, X is —O—, —$CH_2$—, or a bond.

In some embodiments of Formula (I), A is —N—, —CH—, or —C($C_1$-$C_3$ alkyl)-; B is —NH—, —O—, or —S—; X is —O— or —NH—; Y is a bond, —$CH_2$—, or —C(O)—; $R^1$ and $R^2$ are each independently —H; —OH; —$C_1$-$C_6$ alkoxy, optionally substituted with halo (e.g., fluoro); —$C_1$-$C_6$ alkyl, optionally substituted with halo (e.g., fluoro); halo; —CN; or —C(O)N($R_5$)$R_6$; and where $R^3$, $R^4$, $R^5$, and $R^6$ are each —H.

In some embodiments of Formula (I), A is —N—, —CH—, or —C($CH_3$)—; B is —NH—, —O—, or —S—; X is —O—; Y is —$CH_2$— or a bond; $R^1$ and $R^2$ are each independently —H; halo; —CN; —C(O)N($R_5$)$R_6$, or —$OCH_3$ and where $R^3$, $R^4$ are each —H.

In some embodiments of Formula (I), A is —N—, —CH—, or —C($CH_3$)—; B is —NH—, —O—, or —S—; X is —NH—; Y is —$CH_2$— or a bond; $R^1$ and $R^2$ are each independently —H; halo; —CN; —C(O)N($R_5$)$R_6$, or —$OCH_3$ and where $R^3$, $R^4$ are each —H.

In another embodiment, the invention embraces a compound selected from the group consisting of N-(quinuclidin-4-ylmethyl)-1H-indole-3-carboxamide, Quinuclidin-4-ylmethyl 1H-indole-3-carboxylate, N-(quinuclidin-4-ylmethyl)-1H-indazole-3-carboxamide, 5-Fluoro-N-(quinuclidin-4-ylmethyl)-1H-indazole-3-carboxamide, N-(quinuclidin-4-ylmethyl)benzo[d]isothiazole-3-carboxamide, Quinuclidin-4-ylmethyl 5-chloro-1H-indole-3-carboxylate, Quinuclidin-4-ylmethyl 5-cyano-1H-indole-3-carboxylate, Quinuclidin-4-ylmethyl 5-carbamoyl-1H-indole-3-carboxylate, Quinuclidin-4-ylmethyl 2-methyl-1H-indole-3-carboxylate, Quinuclidin-4-ylmethyl 5-methoxy-2-methyl-1H-indole-3-carboxylate, (3-Oxoquinuclidin-4-yl)methyl 1H-indole-3-carboxylate, Quinuclidin-4-ylmethyl 1H-indazole-3-carboxylate, Quinuclidin-4-ylmethyl 5-methoxy-1H-indole-3-carboxylate, Quinuclidin-4-ylmethyl 6-methoxy-1H-indole-3-carboxylate, Quinuclidin-4-ylmethyl 5-(difluoromethoxy)-1H-indole-3-carboxylate, Quinuclidin-4-ylmethyl 6-(difluoromethoxy)-1H-indole-3-carboxylate, Quinuclidin-4-ylmethyl 5-((trifluoromethoxy)methyl)-1H-indole-3-carboxylate, Quinuclidin-4-ylmethyl 5-isopropoxy-1H-indole-3-carboxylate, Quinuclidin-4-ylmethyl 5-(cyclopropylmethoxy)-1H-indole-3-carboxylate, 1-azabicyclo[2.2.1]heptan-4-ylmethyl 1H-indole-3-carboxylate, 1-azabicyclo[2.2.1]heptan-4-ylmethyl 5-fluoro-1H-indole-3-carboxylate, 1-azabicyclo[2.2.1]heptan-4-ylmethyl 5-chloro-1H-indole-3-carboxylate, 1-azabicyclo[2.2.1]heptan-4-ylmethyl 5-methoxy-1H-indole-3-carboxylate, 1-azabicyclo[2.2.1]heptan-4-ylmethyl 5-(difluoromethoxy)-1H-indole-3-carboxylate, 1-azabicyclo[2.2.1]heptan-4-ylmethyl 6-methoxy-1H-indole-3-carboxylate, and 1-azabicyclo[2.2.1]heptan-4-ylmethyl 6-(difluoromethoxy)-1H-indole-3-carboxylate; or a pharmaceutically acceptable salt, isomer, mixtures of isomers, crystalline form, non-crystalline form, hydrate, or solvate thereof.

In another embodiment, the invention embraces a compound selected from the group consisting of N-(quinuclidin-4-ylmethyl)-1H-indole-3-carboxamide, Quinuclidin-4-ylmethyl 1H-indole-3-carboxylate, N-(quinuclidin-4-ylmethyl)-1H-indazole-3-carboxamide, 5-Fluoro-N-(quinuclidin-4-ylmethyl)-1H-indazole-3-carboxamide, Quinuclidin-4-ylmethyl 5-chloro-1H-indole-3-carboxylate, Quinuclidin-4-ylmethyl 5-cyano-1H-indole-3-carboxylate, Quinuclidin-4-ylmethyl 5-carbamoyl-1H-indole-3-carboxylate, Quinuclidin-4-ylmethyl 2-methyl-1H-indole-3-carboxylate, Quinuclidin-4-ylmethyl 5-methoxy-2-methyl-1H-indole-3-carboxylate, (3-Oxoquinuclidin-4-yl)methyl 1H-indole-3-carboxylate, Quinuclidin-4-ylmethyl 1H-indazole-3-carboxylate, Quinuclidin-4-ylmethyl 5-methoxy-1H-indole-3-carboxylate, Quinuclidin-4-ylmethyl 6-methoxy-1H-indole-3-carboxylate, Quinuclidin-4-ylmethyl 5-(difluoromethoxy)-1H-indole-3-carboxylate, Quinuclidin-4-ylmethyl 6-(difluoromethoxy)-1H-indole-3-carboxylate, Quinuclidin-4-ylmethyl 5-((trifluoromethoxy)methyl)-1H-indole-3-carboxylate, Quinuclidin-4-ylmethyl 5-isopropoxy-1H-indole-3-carboxylate, Quinuclidin-4-ylmethyl 5-(cyclopropylmethoxy)-1H-indole-3-carboxylate, 1-azabicyclo[2.2.1]heptan-4-ylmethyl 1H-indole-3-carboxylate, 1-azabicyclo[2.2.1]heptan-4-ylmethyl 5-fluoro-1H-indole-3-carboxylate, 1-azabicyclo[2.2.1]heptan-4-ylmethyl 5-chloro-1H-indole-3-carboxylate, 1-azabicyclo[2.2.1]heptan-4-ylmethyl 5-methoxy-1H-indole-3-carboxylate, 1-azabicyclo[2.2.1]heptan-4-ylmethyl 5-(difluoromethoxy)-1H-indole-3-carboxylate, 1-azabicyclo[2.2.1]heptan-4-ylmethyl 6-methoxy-1H-indole-3-carboxylate, and 1-azabicyclo[2.2.1]heptan-4-ylmethyl 6-(difluoromethoxy)-1H-indole-3-carboxylate; or a pharmaceutically acceptable salt, isomer, mixtures of isomers, crystalline form, non-crystalline form, hydrate, or solvate thereof.

In another embodiment, the invention embraces a compound selected from the group consisting of N-(quinuclidin-4-ylmethyl)-1H-indazole-3-carboxamide, 5-Fluoro-N-(quinuclidin-4-ylmethyl)-1H-indazole-3-carboxamide, N-(quinuclidin-4-ylmethyl)benzo[d]isothiazole-3-carboxamide, and Quinuclidin-4-ylmethyl 1H-indazole-3-carboxylate; or a pharmaceutically acceptable salt, isomer, mixtures of isomers, crystalline form, non-crystalline form, hydrate, or solvate thereof.

In another embodiment, the invention embraces a compound selected from the group consisting of N-(quinuclidin-4-ylmethyl)-1H-indole-3-carboxamide, Quinuclidin-4-ylmethyl 1H-indole-3-carboxylate, N-(quinuclidin-4-ylmethyl)benzo[d]isothiazole-3-carboxamide, Quinuclidin-4-ylmethyl 5-chloro-1H-indole-3-carboxylate, Quinuclidin-4-ylmethyl 5-cyano-1H-indole-3-carboxylate, Quinuclidin-4-ylmethyl 5-carbamoyl-1H-indole-3-carboxylate, Quinuclidin-4-ylmethyl 2-methyl-1H-indole-3-carboxylate, Quinuclidin-4-ylmethyl 5-methoxy-2-methyl-1H-indole-3-carboxylate, (3-Oxoquinuclidin-4-yl)methyl 1H-indole-3-carboxylate, Quinuclidin-4-ylmethyl 5-methoxy-1H-indole-3-carboxylate, Quinuclidin-4-ylmethyl 6-methoxy-1H-indole-3-carboxylate, Quinuclidin-4-ylmethyl 5-(difluoromethoxy)-1H-indole-3-carboxylate, Quinuclidin-4-ylmethyl 6-(difluoromethoxy)-1H-indole-3-carboxylate, Quinuclidin-4-ylmethyl 5-((trifluoromethoxy)methyl)-1H-indole-3-carboxylate, Quinuclidin-4-ylmethyl 5-isopropoxy-1H-indole-3-carboxylate, Quinuclidin-4-ylmethyl 5-(cyclopropylmethoxy)-1H-indole-3-carboxylate, 1-azabicyclo[2.2.1]heptan-4-ylmethyl 1H-indole-3-carboxylate, 1-azabicyclo[2.2.1]heptan-4-ylmethyl 5-fluoro-1H-indole-3-carboxylate, 1-azabicyclo[2.2.1]heptan-4-ylmethyl 5-chloro-1H-indole-3-carboxylate, 1-azabicyclo[2.2.1]heptan-4-ylmethyl 5-methoxy-1H-indole-3-carboxylate, 1-azabicyclo[2.2.1]heptan-4-ylmethyl 5-(difluoromethoxy)-1H-indole-3-carboxylate, 1-azabicyclo[2.2.1]heptan-4-ylmethyl 6-methoxy-1H-indole-3-carboxylate, and 1-azabicyclo[2.2.1]heptan-4-ylmethyl 6-(difluoromethoxy)-1H-indole-3-carboxylate; or a pharmaceutically acceptable salt, isomer, mixtures of isomers, crystalline form, non-crystalline form, hydrate, or solvate thereof.

In another embodiment, the invention embraces a compound selected from the group consisting of N-(quinuclidin-4-ylmethyl)-1H-indazole-3-carboxamide, 5-Fluoro-N-(quinuclidin-4-ylmethyl)-1H-indazole-3-carboxamide, and Quinuclidin-4-ylmethyl 1H-indazole-3-carboxylate; or a pharmaceutically acceptable salt, isomer, mixtures of isomers, crystalline form, non-crystalline form, hydrate, or solvate thereof.

In another embodiment, the invention embraces the compound N-(quinuclidin-4-ylmethyl)benzo[d]isothiazole-3-carboxamide, or a pharmaceutically acceptable salt, isomer, mixtures of isomers, crystalline form, non-crystalline form, hydrate, or solvate thereof.

In another embodiment, the invention embraces a compound selected from the group consisting of N-(quinuclidin-4-ylmethyl)-1H-indole-3-carboxamide, N-(quinuclidin-4-ylmethyl)-1H-indazole-3-carboxamide, 5-fluoro-N-(quinuclidin-4-ylmethyl)-1H-indazole-3-carboxamide, N-(quinuclidin-4-ylmethyl)benzo[d]isothiazole-3-carboxamide, or a pharmaceutically acceptable salt, isomer, mixtures of isomers, crystalline form, non-crystalline form, hydrate, or solvate thereof.

In another embodiment, the invention embraces a compound selected from the group consisting of Quinuclidin-4-ylmethyl 1H-indole-3-carboxylate, Quinuclidin-4-ylmethyl 5-chloro-1H-indole-3-carboxylate, Quinuclidin-4-ylmethyl 5-cyano-1H-indole-3-carboxylate, Quinuclidin-4-ylmethyl 5-carbamoyl-1H-indole-3-carboxylate, Quinuclidin-4-ylmethyl 2-methyl-1H-indole-3-carboxylate, Quinuclidin-4-ylmethyl 5-methoxy-2-methyl-1H-indole-3-carboxylate, (3-Oxoquinuclidin-4-yl)methyl 1H-indole-3-carboxylate, Quinuclidin-4-ylmethyl 1H-indazole-3-carboxylate, Quinuclidin-4-ylmethyl 5-methoxy-1H-indole-3-carboxylate, Quinuclidin-4-ylmethyl 6-methoxy-1H-indole-3-carboxylate, Quinuclidin-4-ylmethyl 5-(difluoromethoxy)-1H-indole-3-carboxylate, Quinuclidin-4-ylmethyl 6-(difluoromethoxy)-1H-indole-3-carboxylate, Quinuclidin-4-ylmethyl 5-((trifluoromethoxy)methyl)-1H-indole-3-carboxylate, Quinuclidin-4-ylmethyl 5-isopropoxy-1H-indole-3-carboxylate, Quinuclidin-4-ylmethyl 5-(cyclopropylmethoxy)-1H-indole-3-carboxylate, 1-azabicyclo[2.2.1]heptan-4-ylmethyl 1H-indole-3-carboxylate, 1-azabicyclo[2.2.1]heptan-4-ylmethyl 5-fluoro-1H-indole-3-carboxylate, 1-azabicyclo[2.2.1]heptan-4-ylmethyl 5-chloro-1H-indole-3-carboxylate, 1-azabicyclo[2.2.1]heptan-4-ylmethyl 5-methoxy-1H-indole-3-carboxylate, 1-azabicyclo[2.2.1]heptan-4-ylmethyl 5-(difluoromethoxy)-1H-indole-3-carboxylate, 1-azabicyclo[2.2.1]heptan-4-ylmethyl 6-methoxy-1H-indole-3-carboxylate, and 1-azabicyclo[2.2.1]heptan-4-ylmethyl 6-(difluoromethoxy)-1H-indole-3-carboxylate; or a pharmaceutically acceptable salt, isomer, mixtures of isomers, crystalline form, non-crystalline form, hydrate, or solvate thereof.

In some embodiments, the compound is quinuclidin-4-ylmethyl 1H-indole-3-carboxylate; or a pharmaceutically acceptable salt, isomer, mixtures of isomers, crystalline form, non-crystalline form, hydrate, or solvate thereof.

In certain embodiments, the invention embraces compounds of Formula (II):

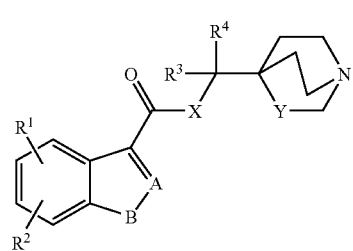

(II)

wherein
A is —N—; —CH—; or —C($C_1$-$C_6$ alkyl)-, optionally substituted with one or more groups selected from hydroxyl and halo;
B is —NH—; —N($C_1$-$C_6$ alkyl)-, optionally substituted with one or more groups selected from hydroxyl and halo; —O—; or —S—;
X is O, $CH_2$, or a bond;
Y is a bond, —$CH_2$—, —$(CH_2)_2$—, —$OCH_2$—, —C(O)—, —CH($OR^7$)—, —C($OR^7$)$_2$—,

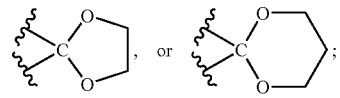

$R^7$ is —$C_1$-$C_6$ alkyl, optionally substituted with one or more groups selected from hydroxyl and halo;
$R^1$ and $R^2$ are each independently —H; —OH; —$C_1$-$C_6$ alkoxy, optionally substituted with one or more groups selected from hydroxyl and halo; —$C_1$-$C_6$ alkyl, optionally substituted with one or more groups selected from hydroxyl and halo; —$C_1$-$C_6$ alkyl-($C_1$-$C_6$ alkoxy), optionally substituted with one or more groups selected from hydroxyl and halo; halo; —$NO_2$; —CN; —C(O)N($R_5$)$R_6$; —S(O)$_2$$R_5$; —S(O)$_2$N($R_5$)$R_6$; or wherein $R^1$ and $R^2$ are at adjacent carbons and together substituted with —O—$CH_2$—O— to form a ring; and
$R^3$, $R^4$, $R^5$, and $R^6$ are each independently —H or —$C_1$-$C_6$ alkyl, optionally substituted with one or more groups selected from hydroxyl and halo;
or a pharmaceutically acceptable salt, isomer, mixtures of isomers, crystalline form, non-crystalline form, hydrate, or solvate thereof.

In some embodiments of Formula (II),
A is —N—; —CH—; or —C($C_1$-$C_3$ alkyl)-;
B is —NH—; —N($C_1$-$C_3$ alkyl)-; —O—; or —S—;
X is —O—; —$CH_2$—; or a bond;
Y is a bond, —$CH_2$—, —$(CH_2)_2$—, —$OCH_2$—, —C(O)—, —CH($OR^7$)—, —C($OR^7$)$_2$—,

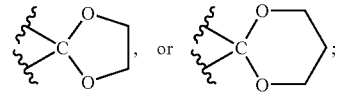

$R^7$ is —$C_1$-$C_3$ alkyl;
$R^1$ and $R^2$ are each independently —H; —OH; —$C_1$-$C_6$ alkoxy, optionally substituted with hydroxyl; $C_1$-$C_6$ alkyl, optionally substituted with hydroxyl; halo; —$NO_2$; —CN;

—C(O)N($R_5$)$R_6$; —S(O)$_2$$R_5$; —S(O)$_2$N($R_5$)$R_6$, —OCF$_3$, —OCHF$_2$, —OCF$_3$; or wherein $R^1$ and $R^2$ are at adjacent carbons and together substituted with —O—CH$_2$—O— to form a ring; and where $R^3$, $R^4$, $R^5$, and $R^6$ are each independently —H or —C$_1$-C$_3$ alkyl;

or a pharmaceutically acceptable salt, isomer, mixtures of isomers, crystalline form, non-crystalline form, hydrate, or solvate thereof.

In some embodiments of Formula (II), A is —N—, —CH—, or —C(CH$_3$)—. In other embodiments, A is —N—. In other embodiments, A is —CH—. In other embodiments, A is —C(C$_1$-C$_3$ alkyl)-. In other embodiments, A is —C(CH$_3$)—. In other embodiments, A is —C(CH$_2$CH$_3$)—. In other embodiments, A is —C(CH$_2$CH$_2$CH$_3$)—. In other embodiments, A is —C(CH(CH$_3$)$_2$)—.

In some of these embodiments of Formula (II), B is —NH—, —O—, or —S—. In other embodiments, B is —NH— or —S—. In other embodiments, B is —NH— or —O—. In other embodiments, B is —O— or —S—. In other embodiments, B is —NH—. In other embodiments, B is —S—. In other embodiments, B is —O—. In other embodiments, B is —N(C$_1$-C$_3$ alkyl)-. In other embodiments, B is —N(CH$_3$)—. In other embodiments, B is —N(CH$_2$CH$_3$)—. In other embodiments, B is —N(CH$_2$CH$_2$CH$_3$)—. In other embodiments, B is —N(CH(CH$_3$)$_2$)—. In other embodiments, B is —O—.

In some of these embodiments of Formula (II), X is —O—. In other embodiments, X is —CH$_2$—. In other embodiments, X is a bond.

In some of these embodiments of Formula (II), Y is —CH$_2$—, —(CH$_2$)$_2$—, —OCH$_2$—, —C(O)—, or a bond. In other embodiments, Y is —CH$_2$—, —(CH$_2$)$_2$—, —C(O)—, or a bond. In other embodiments, Y is —CH$_2$—, —(CH$_2$)$_2$—, or a bond. In other embodiments, Y is —CH$_2$—, —C(O)—, or a bond. In other embodiments, Y is —CH$_2$— or —C(O)—. In other embodiments, Y is —CH$_2$—. In other embodiments, Y is —(CH$_2$)$_2$—. In other embodiments, Y is —OCH$_2$—. In other embodiments, Y is a bond. In other embodiments, Y is —C(O)—. In other embodiments, Y is —CH(O$R^7$)—. In other embodiments, Y is —CH(OCH$_3$)—. In other embodiments, Y is —CH(OCH$_2$CH$_3$)—. In other embodiments, Y is —CH(OCH$_2$CH$_2$CH$_3$)—. In other embodiments, Y is —CH(OCH(CH$_3$)$_2$)—. In other embodiments, Y is —C(O$R^7$)$_2$—. In other embodiments, Y is

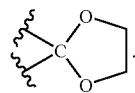

In other embodiments, Y is

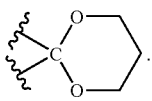

In some of these embodiments of Formula (II), $R^1$ and $R^2$ are each independently —H; —OH; C$_1$-C$_6$ alkyl, optionally substituted with hydroxyl; halo; —NO$_2$; —CN; —C(O)N($R_5$)$R_6$; —S(O)$_2$$R_5$; —S(O)$_2$N($R_5$)$R_6$; —CF$_3$; —OCHF$_2$; —OCF$_3$; or wherein $R^1$ and $R^2$ are together substituted with —O—CH$_2$—O— to form a ring. In other embodiments, $R^1$ and $R^2$ are each independently —H; C$_1$-C$_6$ alkyl, optionally substituted with hydroxyl; halo; —NO$_2$; —CN; —C(O)N($R_5$)$R_6$; —S(O)$_2$$R_5$; —S(O)$_2$N($R_5$)$R_6$; —CF$_3$; —OCHF$_2$; —OCF$_3$; or wherein $R^1$ and $R^2$ are together substituted with —O—CH$_2$—O— to form a ring. In other embodiments, $R^1$ and $R^2$ are each independently —H, —C$_1$-C$_6$ alkyl, halo, —NO$_2$, —CN, —CONH$_2$, or —SO$_2$CH$_3$. In other embodiments, $R^1$ and $R^2$ are each independently —H, C$_1$-C$_3$ alkoxy, —Cl, —CN, or —CONH$_2$. In other embodiments, $R^1$ and $R^2$ are each independently —H, —OCH$_3$, —Cl, —CN, or —CONH$_2$. In other embodiments, $R^1$ and $R^2$ is not —H. In other embodiments, $R^1$ and $R^2$ is —H. In other embodiments, $R^1$ or $R^2$ is —H, and the other is —OCH$_3$, —Cl, —CN, or —CONH$_2$. In other embodiments, $R^1$ or $R^2$ is —H, and the other is —CN or —CONH$_2$. In other embodiments, $R^1$ or $R^2$ is —H, and the other is —OH. In other embodiments, $R^1$ or $R^2$ is —H, and the other is —C$_1$-C$_6$ alkyl, optionally substituted with hydroxyl. In other embodiments, $R^1$ or $R^2$ is —H, and the other is —C$_1$-C$_6$ alkoxy, optionally substituted with hydroxyl. In other embodiments, $R^1$ or $R^2$ is —H, and the other is halo. In other embodiments, $R^1$ or $R^2$ is —H, and the other is —NO$_2$. In other embodiments, $R^1$ or $R^2$ is —H, and the other is —CN. In other embodiments, $R^1$ or $R^2$ is —H, and the other is —C(O)N($R_5$)$R_6$. In other embodiments, $R^1$ or $R^2$ is —H, and the other is —S(O)$_2$$R_5$. In other embodiments, $R^1$ or $R^2$ is —H, and the other is —S(O)$_2$N($R_5$)$R_6$. In other embodiments, $R^1$ or $R^2$ is —H, and the other is —CF$_3$. In other embodiments, $R^1$ or $R^2$ is —H, and the other is —OCHF$_2$. In other embodiments, $R^1$ or $R^2$ is —H, and the other is —OCF$_3$. In other embodiments, $R^1$ or $R^2$ is located at the 5-position and is not —H. In other embodiments, $R^1$ or $R^2$ is 5-OCH$_3$, 5-Cl, 5-CN, or 5-CONH$_2$. In other embodiments, $R^1$ and $R^2$ are not —H. In other embodiments, $R^1$ and $R^2$ are —H. In other embodiments, $R^1$ and $R^2$ are —C$_1$-C$_6$ alkyl. In other embodiments, $R^1$ and $R^2$ are —C$_1$-C$_6$ alkoxy. In other embodiments, $R^1$ and $R^2$ are —OCH$_3$. In other embodiments, $R^1$ and $R^2$ are halo. In other embodiments, $R^1$ and $R^2$ are at adjacent carbons and together substituted with —O—CH$_2$—O— to form a ring.

In some of these embodiments of Formula (II), both $R^5$ and $R^6$ are —H. In other embodiments, both $R^5$ and $R^6$ are —C$_1$-C$_3$ alkyl. In other embodiments, both $R^5$ and $R^6$ are —CH$_3$. In other embodiments, both $R^5$ and $R^6$ are —CH$_2$CH$_3$. In other embodiments, both $R^5$ and $R^6$ are —CH$_2$CH$_2$CH$_3$. In other embodiments, both $R^5$ and $R^6$ are —CH(CH$_3$)$_2$. In other embodiments, one of $R^5$ or $R^6$ is —H, and the other is —C$_1$-C$_3$ alkyl. In other embodiments, one of $R^5$ or $R^6$ is —H, and the other is —CH$_3$. In other embodiments, one of $R^5$ or $R^6$ is —H, and the other is —CH$_2$CH$_3$. In other embodiments, one of $R^5$ or $R^6$ is —H, and the other is —CH$_2$CH$_2$CH$_3$. In other embodiments, one of $R^5$ or $R^6$ is —H, and the other is —CH(CH$_3$)$_2$.

In some of these embodiments of Formula (II), at least one of $R^3$ and $R^4$ is —H. In other embodiments, at least one of $R^3$ and $R^4$ is not —H. In other embodiments, both $R^3$ and $R^4$ are —H. In other embodiments, n both $R^3$ and $R^4$ are —C$_1$-C$_3$ alkyl. In other embodiments, one of $R^3$ or $R^4$ is —H, and the other is —CH$_3$. In other embodiments, one of $R^3$ or $R^4$ is —H, and the other is —CH$_2$CH$_3$. In other embodiments, one of $R^3$ or $R^4$ is —H, and the other is —CH$_2$CH$_2$CH$_3$. In other embodiments, one of $R^3$ or $R^4$ is —H, and the other is —CH(CH$_3$)$_2$.

Some of these embodiments of Formula (II), have the proviso that when A is —N— or —CH—, B is —NH— or —N(C$_1$-C$_3$ alkyl)-, X is —O—, Y is —CH$_2$—, $R^3$ and $R^4$ are —H, and one of $R^1$ and $R^2$ is —H, then the other of $R^1$ and $R^2$ is not alkoxy.

Some of these embodiments of Formula (II), have the proviso that when A is —N— or —CH—, B is —NH— or —N(C$_1$-C$_3$ alkyl)-, X is —O—, Y is —CH$_2$—, R$^3$ and R$^4$ are —H, and one of R$^1$ and R$^2$ is —H, then the other of R$^1$ and R$^2$ is not 7-alkoxy.

Some of these embodiments of Formula (II), have the proviso that when A is —N— or —CH—, B is —NH— or —N(C$_1$-C$_3$ alkyl)—, X is —O—, Y is —CH$_2$—, R$^3$ and R$^4$ are —H, and one of R$^1$ and R$^2$ is —H, then the other of R$^1$ and R$^2$ is not 7-OH or 7-alkoxy.

TABLE 1

Exemplary Quinuclidine Compounds

| Compound No. | A | B | X | Y | R$^1$/R$^2$ | R$^3$/R$^4$ |
|---|---|---|---|---|---|---|
| 1 | N | S | NH | CH$_2$ | H/H | H/H |
| 2 | CH | NH | O | CH$_2$ | H/5-Cl | H/H |
| 3 | CH | NH | O | CH$_2$ | H/5-CN | H/H |
| 4 | CH | NH | O | CH$_2$ | H/5-C(O)NH$_2$ | H/H |
| 5 | C—CH$_3$ | NH | O | CH$_2$ | H/H | H/H |
| 6 | C—CH$_3$ | NH | O | CH$_2$ | H/5-OCH$_3$ | H/H |
| 7 | CH | NH | O | C=O | H/H | H/H |
| 8 | CH | NH | NH | CH$_2$ | H/H | H/H |
| 9 | CH | NH | O | CH$_2$ | H/H | H/H |
| 10 | N | NH | NH | CH$_2$ | H/H | H/H |
| 11 | N | NH | NH | CH$_2$ | H/5-F | H/H |
| 12 | N | NH | O | CH$_2$ | H/H | H/H |
| 13 | CH | NH | O | CH$_2$ | H/5-OCH$_3$ | H/H |
| 14 | CH | NH | O | CH$_2$ | H/6-OCH$_3$ | H/H |
| 15 | CH | NH | O | CH$_2$ | H/5-OCHF$_2$ | H/H |
| 16 | CH | NH | O | CH$_2$ | H/6-OCHF$_2$ | H/H |
| 17 | CH | NH | O | CH$_2$ | H/5-CH$_2$OCF$_3$ | H/H |
| 18 | CH | NH | O | CH$_2$ | H/5-OiPr | H/H |
| 19 | CH | NH | O | CH$_2$ | H/5-OCH$_2$cyclopropyl | H/H |
| 20 | CH | NH | O | bond | H/H | H/H |
| 21 | CH | NH | O | bond | H/5-F | H/H |
| 22 | CH | NH | O | bond | H/5-Cl | H/H |
| 23 | CH | NH | O | bond | H/5-OMe | H/H |
| 24 | CH | NH | O | bond | H/5-OCHF$_2$ | H/H |
| 25 | CH | NH | O | bond | H/6-OMe | H/H |
| 26 | CH | NH | O | bond | H/6-OCHF$_2$ | H/H |

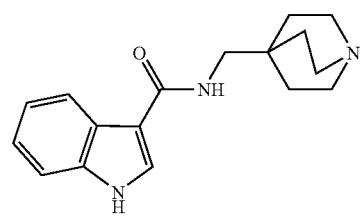

(1): quinuclidin-4-ylmethyl 1H-indole-3-carboxamide;

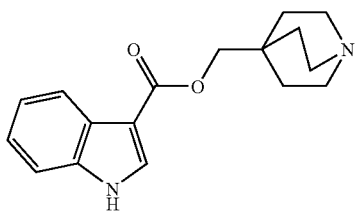

(2): quinuclidin-4-ylmethyl 1H-indole-3-carboxylate;

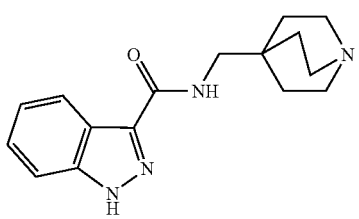

(3): N-(quinuclidin-4-ylmethyl)-1H-indazole-3-carboxamide;

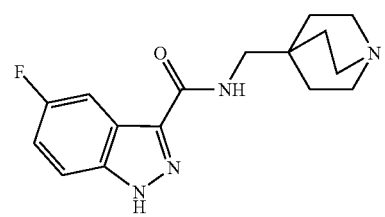

(4): 5-fluoro-N-(quinuclidin-4-ylmethyl)-1H-indazole-3-carboxamide;

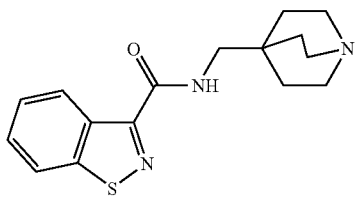

(5): N-(quinuclidin-4-ylmethyl)benzo[d]isothiazole-3-carboxamide;

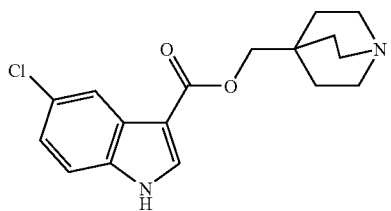

(6): quinuclidin-4-ylmethyl 5-chloro-1H-indole-3-carboxylate;

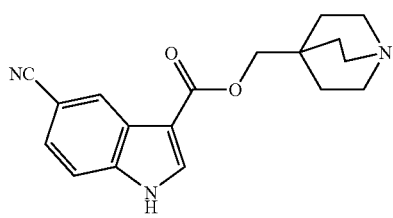

(7): quinuclidin-4-ylmethyl 5-cyano-1H-indole-3-carboxylate;

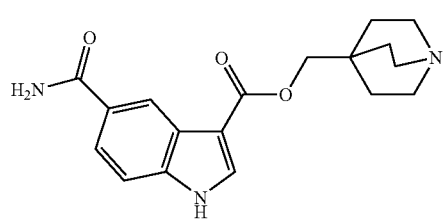

(8): quinuclidin-4-ylmethyl 5-carbamoyl-1H-indole-3-carboxylate;

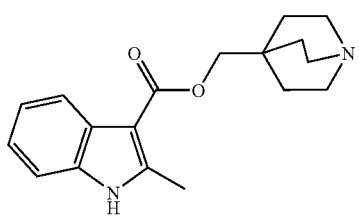

(9): quinuclidin-4-ylmethyl 2-methyl-1H-indole-3-carboxylate;

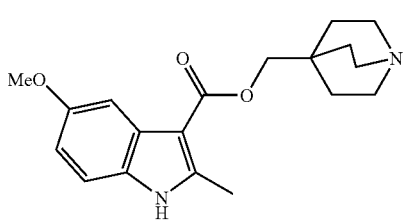

(10): quinuclidin-4-ylmethyl 5-methoxy-2-methyl-1H-indole-3-carboxylate;

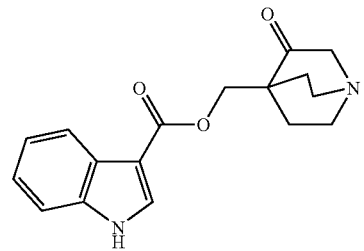

(11): (3-oxoquinuclidin-4-yl)methyl 1H-indole-3-carboxylate;

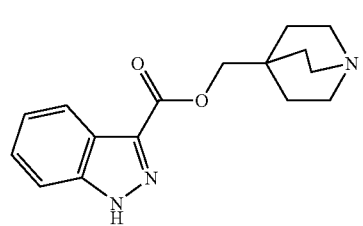

(12): quinuclidin-4-ylmethyl 1H-indazole-3-carboxylate;

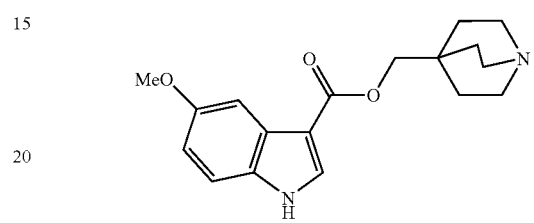

(13): quinuclidin-4-ylmethyl 5-methoxy-1H-indole-3-carboxylate;

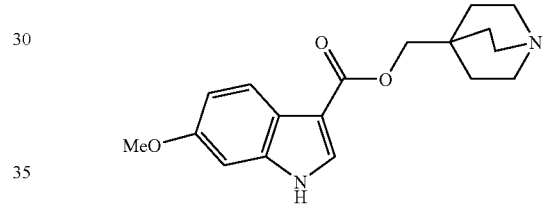

(14): quinuclidin-4-ylmethyl 6-methoxy-1H-indole-3-carboxylate;

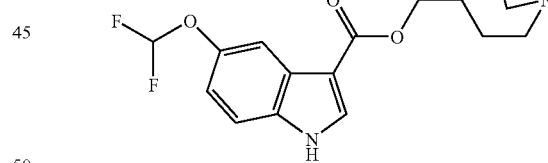

(15): quinuclidin-4-ylmethyl 5-(difluoromethoxy)-1H-indole-3-carboxylate;

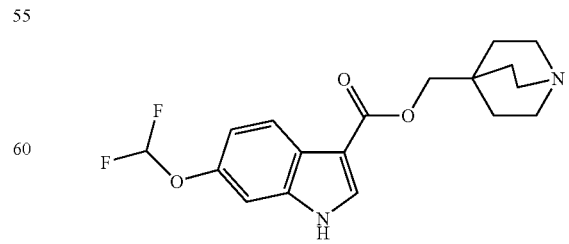

(16): quinuclidin-4-ylmethyl 6-(difluoromethoxy)-1H-indole-3-carboxylate;

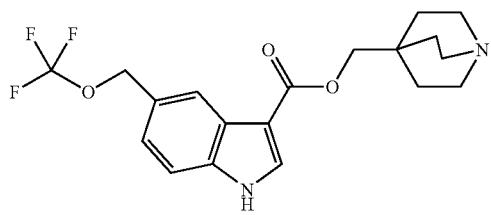

(17): quinuclidin-4-ylmethyl 5-((trifluoromethoxy)methyl)-1H-indole-3-carboxylate;

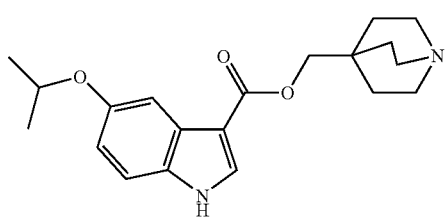

(18): quinuclidin-4-ylmethyl 5-isopropoxy-1H-indole-3-carboxylate;

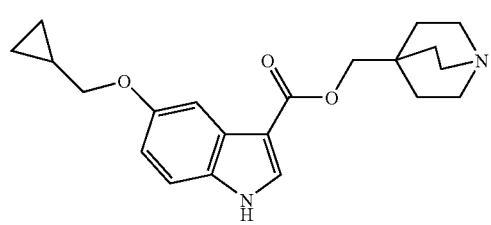

(19): quinuclidin-4-ylmethyl 5-(cyclopropylmethoxy)-1H-indole-3-carboxylate;

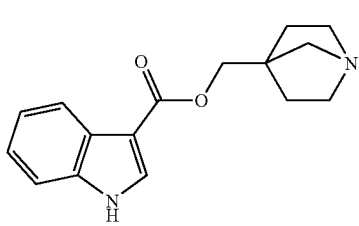

(20): 1-azabicyclo[2.2.1]heptan-4-ylmethyl 1H-indole-3-carboxylate;

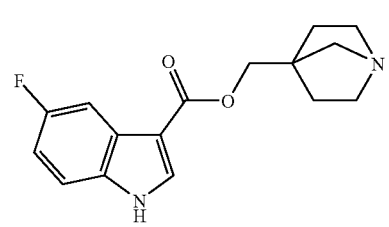

(21): 1-azabicyclo[2.2.1]heptan-4-ylmethyl 5-fluoro-1H-indole-3-carboxylate;

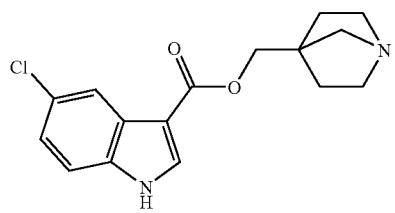

(22): 1-azabicyclo[2.2.1]heptan-4-ylmethyl 5-chloro-1H-indole-3-carboxylate;

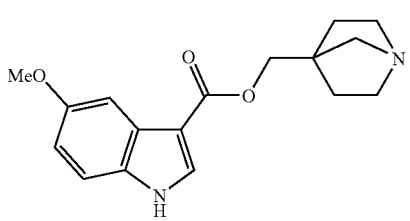

(23): 1-azabicyclo[2.2.1]heptan-4-ylmethyl 5-methoxy-1H-indole-3-carboxylate;

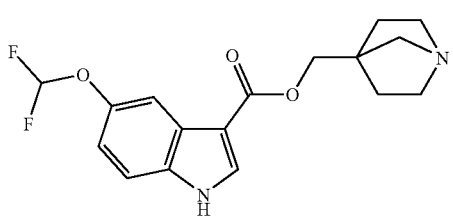

(24): 1-azabicyclo[2.2.1]heptan-4-ylmethyl 5-(difluoromethoxy)-1H-indole-3-carboxylate;

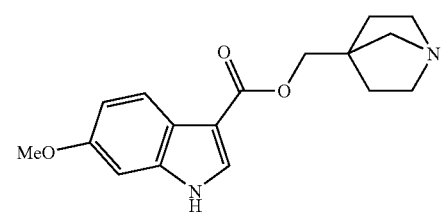

(25): 1-azabicyclo[2.2.1]heptan-4-ylmethyl 6-methoxy-1H-indole-3-carboxylate;

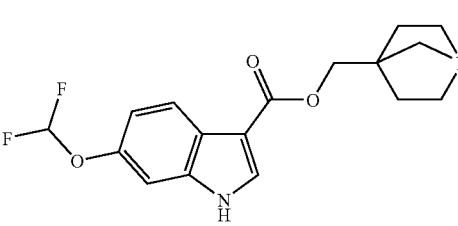

(26): 1-azabicyclo[2.2.1]heptan-4-ylmethyl 6-(difluoromethoxy)-1H-indole-3-carboxylate.

Stereochemical, enantiomeric, diastereomeric, conformeric, rotomeric, tautomeric, solvate, hydrate, polymorphic, crystalline form, non-crystalline form, salt, pharmaceutically acceptable salt, metabolite and prodrug variations of the compounds above may also be used in the invention, provided that they have the α7-nAChR mediation characteristics as described herein.

Synthetic Methods

The compounds of the invention can be readily synthesized by a variety of synthetic methods commonly known in the art. The discussion below is offered to illustrate certain of the diverse methods available for use in assembling the compounds of the invention. However, the discussion is not intended to define the scope of the reactions or reaction sequences that are useful in preparing the compounds of the invention.

Compounds where X=N-alkyl are made by coupling of the appropriate aromatic bicycle (e.g., indole, indazole, benzisoxazole, benzisothiazole, benzofuran or benzothiophene) containing a carbonyl chloride with the appropriate secondary amine (prepared, e.g., by reductive amination of formaldehyde, acetaldehyde, or propionaldehyde with (quinuclidin-4-yl)methanamine) in the presence of sodium cyanoborohydride.

Compounds where X=$CH_2$ or a bond are prepared by Lewis acid-catalyzed acylation of the appropriate aromatic bicycle (e.g., indole, indazole, benzisoxazole, benzisothiazole, benzofuran or benzothiophene) with the appropriately substituted propanoyl chloride (e.g., 3-(quinuclidin-4-yl)propionylchloride) or appropriately substituted acetyl chloride (e.g., 2-(quinuclidin-4-yl)acetyl chloride), respectively.

3-(Quinuclidin-4-yl)propionylchloride may be synthesized from (quinuclidin-4-yl)methanol (vide supra) by oxidation to the aldehyde, condensation with triethyl phosphonoacetate in the presence of a base such as sodium hydride (Homer-Emmons reaction), hydrogenating the resulting 3-(4-quinuclidinyl)crotonate over Pd/C catalyst, hydrolyzing the ester group, and converting the resulting acid to the acid chloride with oxalyl chloride in dichloromethane containing a catalytic amount of dimethylformamide.

2-(Quinuclidin-4-yl)acetyl chloride may be made by converting (quinuclidin-4-yl)methanol (vide supra) to the mesylate (methanesulfonylchloride/triethylamine in chloroform) which is then treated with sodium cyanide in dimethylformamide to form (quinuclidin-4-yl)acetonitrile. Heating this in ethanol saturated with hydrogen chloride gas produces the corresponding ethyl ester which is hydrolyzed to the acid by treatment with 6N hydrochloric acid. Finally, the acid is converted to the acid chloride as described above.

Alternatively, 3-(quinuclidin-4-yl)propionylchloride or 2-(quinuclidin-4-yl)acetyl chloride can be treated with dimethylamine to form the corresponding dimethylamides, which will acylate indoles under the influence of phosphorous oxychloride in an inert solvent such as 1,2-dichloroethane.

Inhibition of α7-AChNR

The compounds and formulations thereof described herein may be capable of interacting with (e.g., reducing) α7-nicotinic acetylcholine receptor (α7-nAChR) activity. In one aspect, is provided a method of reducing α7-nicotinic acetylcholine receptor (α7-nAChR) activity, the method comprising contacting an α7-nicotinic acetylcholine receptor with an effective amount of a compound described herein (e.g., a compound of Formula I, II, and/or any compound of Table 1), or a pharmaceutically acceptable salt or solvate thereof. In some variations, the α7-nicotinic acetylcholine receptor is contacted in a cell. In some embodiments, the cell is contacted in vivo. In some embodiments, the cell is contacted in vitro. α7-nicotinic acetylcholine receptor may be contacted in any suitable environment or any suitable sample. For example, the α7-nicotinic acetylcholine receptor may be contacted in vitro, within a cell, or within an individual (e.g., a mammal, such as a human). Typically, in vitro solutions are selected such that the components do not substantially interfere with the α7-nicotinic acetylcholine receptor (e.g., aqueous solutions). In some embodiments, the in vitro solution includes a biological sample, such as a mammalian sample. Exemplary mammalian samples include plasma or serum samples and tissue samples, such as a brain biopsy. Any appropriate cell or cellular sample may be selected in which to contact the α7-nicotinic acetylcholine receptor with the compound. Exemplary cells include human embryonic kidney (HEK293) cells, HeLa cells, Chinese hamster ovary cells, or neuroblastoma line M17 cells Hela cells, 293 cells.

Conditions Mediated by α7-AChNR

Compounds and formulations discussed herein may be useful for treatment or prevention of a condition mediated by or characterized by α7-nAChR. As used herein, "treatment or prevention of a condition mediated by the α7-nAChR" indicates administering one or more of the compounds discussed herein, with or without additional pharmaceutical agents, in order to reduce, eliminate, and/or prevent either the condition or one or more symptoms of the condition, or to retard the progression of the disease or of one or more symptoms of the condition, or to reduce the severity of the disease or of one or more symptoms of the condition.

Conditions which can be treated or prevented with the compounds and methods of the invention include, but are not limited to neurodegeneration associated with Alzheimer's disease, pre-senile dementia (mild cognitive impairment), or senile dementia, schizophrenia, cognitive deficits associated with schizophrenia, psychosis, cognitive deficits associated with psychosis, attention deficit disorder, attention deficit hyperactivity disorder (ADHD), mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, depression, general anxiety disorder, age-related macular degeneration, Parkinson's disease, tardive dyskinesia, Pick's disease, post traumatic stress disorder, dysregulation of food intake including bulemia and anorexia nervosa, withdrawal symptoms associated with smoking cessation and dependent drug cessation, Tourette's syndrome, glaucoma, neurodegeneration associated with glaucoma, symptoms associated with pain, pain and inflammation, TNF-α related conditions, rheumatoid arthritis, rheumatoid spondylitis, muscle degeneration, osteoporosis, osteoarthritis, psoriasis, contact dermatitis, bone resorption diseases, atherosclerosis, Paget's disease, uveitis, gouty arthritis, inflammatory bowel disease, adult respiratory distress syndrome (ARDS), Crohn's disease, rhinitis, ulcerative colitis, anaphylaxis, asthma, Reiter's syndrome, tissue rejection of a graft, ischemia reperfusion injury, stroke, multiple sclerosis, cerebral malaria, sepsis, septic shock, toxic shock syndrome, fever and myalgias due to infection, HIV-1, HIV-2, and HIV-3, cytomegalovirus (CMV), influenza, adenovirus, a herpes virus (including HSV-1, HSV-2), a herpes zoster, cancer (multiple myeloma, acute and chronic myelogenous leukemia, or cancer-associated cachexia), diabetes (pancreatic beta cell destruction, type I diabetes, or type II diabetes), wound healing (healing burns, and wounds in general including from surgery), bone fracture healing, ischemic heart disease, tinnitus, and stable angina pectoris in a mammal. In some embodiments, 128.

The method of claim 127, wherein the condition is one or more of the cognitive and attention deficiency symptoms associated with Alzheimer's disease, neurodegeneration associated with Alzheimer's disease, pre-senile dementia (mild cognitive impairment), or senile dementia, schizophrenia, cognitive deficits associated with schizophrenia, psychosis, cognitive deficits associated with psychosis, attention deficit disorder, attention deficit hyperactivity disorder (ADHD), mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, depression, general anxiety disorder, age-related macular degeneration, Parkinson's disease, tardive dyskinesia, Pick's disease, post traumatic stress disorder, dysregulation of food intake including bulemia and anorexia nervosa, withdrawal symptoms associated with smoking cessation and dependent drug cessation, or Tourette's syndrome.

Formulations

The compounds described herein can be in formulations (including pharmaceutical compositions) by formulation with additives such as excipients (e.g., one or more excipients), antioxidants (e.g., one or more antioxidants), stabilizers (e.g., one or more stabilizers), preservatives (e.g., one or more preservatives), pH adjusting and buffering agents (e.g., one or more pH adjusting and/or buffering agents), tonicity adjusting agents (e.g., one or more tonicity adjusting agents), thickening agents (e.g., one or more thickening agents), suspending agents (e.g., one or more suspending agents), binding agents (e.g., one or more binding agents, viscosity-increasing agents (e.g., one or more viscosity-increasing agents), and the like, provided that the additional components are pharmaceutically acceptable for the particular condition to be treated. In some embodiments, the formulation may include combinations of two or more of the additional components as described herein (e.g., 2, 3, 4, 5, 6, 7, 8, or more additional components). In some embodiments, the additives include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

The formulations may vary according to the condition to be treated, the amount of compound to be administered, the condition of the individual, and other variables that will readily be apparent to one of ordinary skill in the art in view of the teachings provided herein.

In some embodiments, the pH of the formulations may be from about 3.5 to about 9.5, or from about 4.5 to about 7.5.

Administration and Dosage

The formulations comprising one or more compounds described herein may be administered in conjunction with one or more of the pharmaceutical agents as described herein and as known in the art, including one or more additional pharmaceutical agents to further reduce the occurrence and/or severity of symptoms and/or clinical manifestations thereof, as well as pharmaceutical agents that treat or prevent the underlying conditions, or in conjunction with (e.g., prior to, concurrently with, or after) additional treatment modalities. The formulations as described herein may be administered before, concurrently with, or after the administration of one or more of the pharmaceutical agents described herein. The compounds described herein may also be administered in conjunction with (e.g., prior to, concurrently with, or after) agents to alleviate the symptoms associated with either the condition or the treatment regimen.

In some embodiments, the pharmaceutical agent(s) may be an acetylcholinesterase inhibitor (e.g., donepezil, rivastigmine, or galantamine), an antipsychotic agent (e.g., aripiprazole, ziprasidone, zotepine, risperidone, quetiapine, clozapine, thiothixene, thioridazine, loxapine, haloperidol, fluphenazine, chlorpromazine), or an NMDA antagonist (e.g., memantine). Combinations of two or more of the foregoing may also be formulated, as can be determined by the skilled artisan in view of the teaching provide herein.

As will be well appreciated by the skilled artisan, for particular conditions, different pharmaceutical agent(s) and/or additional treatment modality(ies) may be indicated.

The formulations and methods described herein may be used alone or in conjunction with (e.g., prior to, concurrently with, or after) other modes of treatments (e.g., adjunctive therapy with additional pharmaceutical agents described herein with reference to pharmaceutical formulations of the claimed compounds or known to the skilled artisan) used to treat or prevent the condition being treated/prevented and/or administration of an additional treatment modality, or combinations of the foregone). For example, in combination with one or more additional pharmaceutical agents as described herein and known to those of skill in the art and/or currently available treatment modalities, including, for example, psychotherapy in the treatment of psychological disorders (e.g., schizophrenia), occupational therapy (e.g., to assist in the prevention or slow the rate of loss of memory, etc.). As used herein, the term "additional treatment modality" refers to treatment/prevention of the conditions described herein without the use of a pharmaceutical agent (e.g., psychotherapy, occupational therapy, etc.). Where combinations of pharmaceutical agent(s) and/or additional treatment modality(ies) are used, they may be, independently, administered prior to, concurrently with, or after administration of one or more of the quinuclidine compound(s) (or formulation(s) thereof) as described herein.

The optimal combination of one or more additional treatment modalities and/or additional pharmaceutical agents in conjunction with administration of the formulations described herein, can be determined by an attending physician or veterinarian based on the individual and taking into consideration the various factors effecting the particular individual, including those described herein.

The formulations described herein will generally be used in an amount effective to achieve the intended result, for example in an amount effective to treat or prevent the particular condition being treated or prevented. The formulations may be administered therapeutically to achieve therapeutic benefit. By therapeutic benefit is meant eradication or amelioration of the underlying condition being treated and/or eradication or amelioration of one or more of the symptoms associated with the underlying condition such that the individual reports an improvement in feeling or condition, notwithstanding that the individual may still be afflicted with the underlying condition. Therapeutic benefit also includes halting or slowing the progression of the condition, regardless of whether improvement is realized.

The amount of the formulation administered in order to administer an effective amount will depend upon a variety of factors, including, for example, the particular condition being treated, the frequency of administration, the particular formulation being administered, the severity of the condition being treated and the age, weight and general health of the individual, the adverse effects experienced by the individual being treated, etc. Determination of an effective dosage is within the capabilities of those skilled in the art, particularly in view of the teachings provided herein.

Dosages may also be estimated using in vivo animal models.

The compounds of the invention may be administered enterally (e.g., orally or rectally), parenterally (e.g., sublingually, or inhalation (e.g. as mists or sprays)), or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques.

The compounds are mixed with pharmaceutically acceptable carriers, adjuvants, and vehicles appropriate for the desired route of administration. In some embodiments, the route of administration is orally. In other embodiments, formulations are suitable for oral administration. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The route of administration may vary according to the condition to be treated. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at room temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such formulations may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present formulations in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq (1976).

The compounds can be administered in prodrug form. Prodrugs are derivatives of the compounds which are themselves relatively inactive, but which convert into the active compound when introduced into the individual in which they are used, by a chemical or biological process in vivo, such as an enzymatic conversion. Suitable prodrug formulations include, but are not limited to, peptide conjugates of the compounds of the invention and esters of compounds of the inventions. Further discussion of suitable prodrugs is provided in H. Bundgaard, Design of Prodrugs, New York: Elsevier, 1985; in R. Silverman, The Organic Chemistry of Drug Design and Drug Action, Boston: Elsevier, 2004; in R. L. Juliano (ed.), Biological Approaches to the Controlled Delivery of Drugs (Annals of the New York Academy of Sciences, v. 507), New York: New York Academy of Sciences, 1987; and in E. B. Roche (ed.), Design of Biopharmaceutical Properties Through Prodrugs and Analogs (Symposium sponsored by Medicinal Chemistry Section, APhA Academy of Pharmaceutical Sciences, November 1976 national meeting, Orlando, Fla.), Washington: The Academy, 1977.

The frequency and duration of administration of the formulation will depend on the condition being treated, the condition of the individual, and the like. The formulation may be administered to the individual one or more times, for example, 2, 3, 4, 5, 10, 15, 20, or more times. The formulation may be administered to the individual, for example, once a day, 2 times a day, 3 times a day, or more than 3 times a day. The formulation may also be administered to the individual, for example, less than once a day, for example, every other day, every third day, every week, or less frequently. The formulation may be administered over a period of days, weeks, or months.

The amount of active ingredient that may be combined with the carrier materials to produce a single dosage form will vary depending upon the host to which the active ingredient is administered and the particular mode of administration. It will be understood, however, that the specific dose level for any particular individual will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The pharmaceutical unit dosage chosen is usually fabricated and administered to provide a defined final concentration of drug in the blood, tissues, organs, or other targeted region of the body. The therapeutically effective amount for a given situation can be readily determined by routine experimentation and is within the skill and judgment of the ordinary clinician.

Examples of dosages which can be used are a therapeutically effective amount within the dosage range of about 0.1 µg/kg to about 300 mg/kg, or within about 1.0 µg/kg to about 40 mg/kg body weight, or within about 1.0 µg/kg to about 20 mg/kg body weight, or within about 1.0 µg/kg to about 10 mg/kg body weight, or within about 10.0 µg/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight. Compounds of the present invention may be administered in a single daily dose, or the total daily dosage may be administered in divided dosage of two, three or four times daily.

For topical application, the formulation may be administered, for example transdermally at about 1 mg to about 500 mg, 5 mg to about 100 mg, or 10 mg to about 50 mg (e.g., over 12, 24, or 48 hours).

For IV administration, the formulation may be administered at a dosage of, for example, from about 0.1 mg per day to about 500 mg per day, from about 0.1 mg per day to about 150 mg per day, from about 1 mg per day to about 50 mg per day, or from about 5 mg per day to about 25 mg per day.

For oral administration, the formulation may be administered at a dosage of, for example, from about 0.5 mg per day to about 2000 mg per day, from about 1 mg per day to about 1500 mg per day, from about 5 mg per day to about 1000 mg per day, from about 10 mg per day to about 500 mg per day, or from about 25 mg per day to about 100 mg per day.

When additional active agents are used in combination with the compounds of the present invention, the additional active agents may generally be employed in therapeutic amounts as indicated in the Physicians' Desk Reference (PDR) 53rd Edition (1999), which is incorporated herein by reference, or such therapeutically useful amounts as would be known to one of ordinary skill in the art.

The compounds of the invention and the other therapeutically active agents can be administered at the recommended maximum clinical dosage or at lower doses. Dosage levels of the active compounds in the formulations of the invention may be varied so as to obtain a desired therapeutic response depending on the route of administration, severity of the disease and the response of the individual. When administered in combination with other pharmaceutical agents, the pharmaceutical agents can be formulated as separate formulations that are given at the same time or different times, or the pharmaceutical agents can be given as a single formulation.

Kits

The invention also provides articles of manufacture and kits containing materials useful for the treatment or prevention of a condition mediated by the α7-nAChR. The article of manufacture may comprise a container with a label. Suitable containers include, for example, bottles, vials, and test tubes. The containers may be formed from a variety of materials such as glass or plastic. The container may hold a formulation having an active agent which is effective in treating or preventing conditions mediated by α7-nAChR. The active agent in the formulation is one or more of the compounds of the invention. The label on the container may indicate that the formulation is used for treating or suppressing conditions mediated by α7-nAChR, and may also indicate directions for either in vivo or in vitro use, such as those described above.

The invention also provides kits comprising any one or more of the compounds of the invention. In some embodiments, the kit of the invention comprises the container described above. In other embodiments, the kit of the invention comprises the container described above and a second container comprising a buffer. It may further include other materials desirable from a commercial and user standpoint, including other buffers, diluents, filters, needles, syringes, and package inserts with instructions for performing any methods described herein.

In other aspects, the kits may be used for any of the methods described herein, including, for example, to treat an individual with one or more conditions mediated by or characterized by α7-nAChR, or to suppress one or more conditions mediated by or characterized In certain embodiments the kits may include a dosage amount of at least one formulation as disclosed herein. Kits may also comprise a means for the delivery of the formulation thereof.

The kits may include other pharmaceutical agents for use in conjunction with the formulation described herein. In some variations, the pharmaceutical agent(s) may be one or more anti-psychotic drug. These agents may be provided in a separate form, or mixed with the compounds of the present invention, provided such mixing does not reduce the effectiveness of either the pharmaceutical agent or formulation described herein and is compatible with the route of administration. Similarly the kits may include additional agents for adjunctive therapy or other agents known to the skilled artisan as effective in the treatment or prevention of the conditions described herein.

The kits may optionally include appropriate instructions for preparation and administration of the formulation, side effects of the formulation, and any other relevant information. The instructions may be in any suitable format, including, but not limited to, printed matter, videotape, computer readable disk, optical disc or directions to internet-based instructions.

In another aspect of the invention, kits for treating an individual who suffers from or is susceptible to the conditions described herein are provided, comprising a first container comprising a dosage amount of a composition as disclosed herein, and instructions for use. The container may be any of those known in the art and appropriate for storage and delivery of intravenous formulation. In certain embodiments the kit further comprises a second container comprising a pharmaceutically acceptable carrier, diluent, adjuvant, etc. for preparation of the formulation to be administered to the individual.

Kits may also be provided that contain sufficient dosages of the compounds described herein (including formulations thereof) to provide effective treatment for an individual for an extended period, such as 1-3 days, 1-5 days, a week, 2 weeks, 3, weeks, 4 weeks, 6 weeks, 8 weeks, 3 months, 4 months, 5 months, 6 months, 7 months, 8 months, 9 months or more.

Kits may also include multiple doses of the formulation and instructions for use and packaged in quantities sufficient for storage and use in pharmacies, for example, hospital pharmacies and compounding pharmacies.

The kits may include the composition as described herein packaged in either a unit dosage form or in a multi-use form. The kits may also include multiple units of the unit dose form.

In certain embodiments, are provided a formulation described herein in a unit dose form. In other embodiments a formulation may be provided in a multi-dose form (e.g., a blister pack, etc.).

The invention is further illustrated by the following non-limiting examples.

EXAMPLES

All solvents (reagent grade) were purchased from either Sigma-Aldrich or Fisher Scientific and were used without further purification.

Example 1

(Quinuclidin-4-yl)methanol

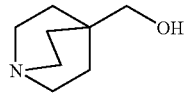

(Quinuclidin-4-yl)carboxylic acid was prepared from 4-cyanoquinuclidine (Oakwood Products) following the procedure of Grob and Renk, *Helv. Chim. Acta,* 37, 1681 (1954).

To a stirred suspension of quinuclidine-4-carboxylic acid hydrochloride (100 mg, 0.523 mmol) in 3 mL of anhydrous tetrahydrofuran at 0° C. was added borane methylsulfide complex (42 mg, 0.553 mmol). The mixture was stirred at room temperature for 1 hr and heated to reflux overnight. The reaction was cooled to 0° C. and carefully treated with 1 mL of methanol. The solvent was then removed under reduced pressure to leave the desired alcohol. Yield 36 mg. MS (m/e): 141.

Example 2

(Quinuclidin-4-yl)methanamine

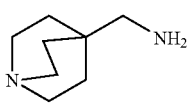

(Quinuclidin-4-yl)methanamine was prepared from 4-cyanoquinuclidine (Oakwood Products) following the procedure of Grob and Renk, *Helv. Chim. Acta.* 61, 1588 (1978).

Example 3

4-(Hydroxymethyl)quinuclidin-3-one

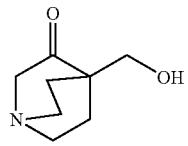

4-(Hydroxymethyl)quinuclidin-3-one was prepared in six steps from N-benzyl-4-acetylpiperidine as described in *J. Org. Chem.* 31, 1053 (1965).

Example 4

1-Azabicyclo[2.2.1]heptan-4-ylmethanol

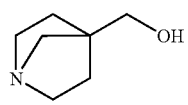

1-Azabicyclo[2.2.1]heptan-4-ylmethanol was prepared by reducing ethyl 1-azabicyclo[2.2.1]heptane-4-carboxylate with lithium aluminum hydride, as described in *J. Med. Chem.* 35, 2392 (1992).

Example 5

1-Azabicyclo[2.2.1]heptan-4-ylmethanamine

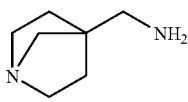

1-Azabicyclo[2.2.1]heptan-4-ylmethanamine was prepared by treatment of ethyl 1-azabicyclo[2.2.1]heptane-4-carboxylate with ammonium chloride and trimethylaluminum and reducing the resulting amide with lithium aluminum hydride.

Example 6

5-(difluoromethoxy)-1H-indole-3-carboxylic acid

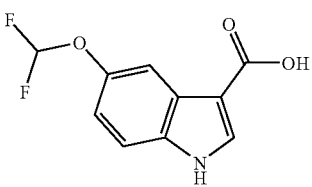

5-Difluoromethoxyindole (PCT 2007/096395) was formylated in the 3-position using a Vilsmeyer-Haack protocol (phosphorous oxychloride/DMF). The resulting aldehyde was oxidized with sodium chlorite/sodium dihydrogen phosphate in aqueous dioxane. MS (m/e) 227.

Example 7

6-(difluoromethoxy)-1H-indole-3-carboxylic acid

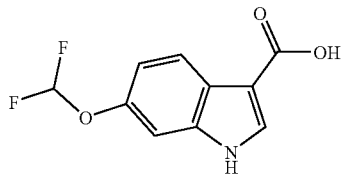

Prepared as for 5-(difluoromethoxy)-1H-indole-3-carboxylic acid starting with 6-difluoromethoxyindole (WO 97/45408 A1). MS (m/e) 227.

Example 8

5-(2,2,2-trifluoroethoxy)-1H-indole-3-carboxylic acid

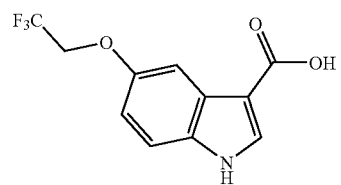

5-(2,2,2-trifluoroethoxy)-1H-indole-3-carboxylic acid was prepared following the procedure reported in Synthesis (1980) 727. 3-methyl-4-nitrophenol (Aldrich) was deprotonated with sodium hydride in HMPA and the resulting phenolate alkylated with 2,2,2-trifluoroethyl tosylate (Aldrich). The resulting trifluoroethyl ether was then converted to the indole using the Batcho-Leimgruber protocol. Formylation and oxidation as described in herein gave the title compound as an off-white solid. MS (m/e) 260.

Example 9

5-isopropoxy-1H-indole-3-carboxylic acid

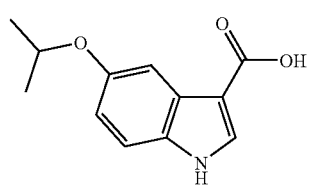

5-isopropoxy-1H-indole-3-carboxylic acid was prepared in a similar manner as described in the examples above MS (m/e) 219.

Example 10

5-(cyclopropylmethoxy)-1H-indole-3-carboxylic acid

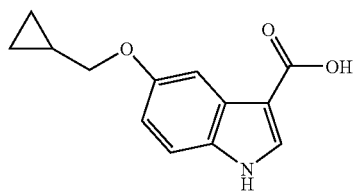

5-(cyclopropylmethoxy)-1H-indole-3-carboxylic acid was prepared in a similar manner as described in the examples above MS (m/e) 231.

Example 11

(Quinuclidin-4-yl)methyl 1H-indole-3-carboxylate (2)

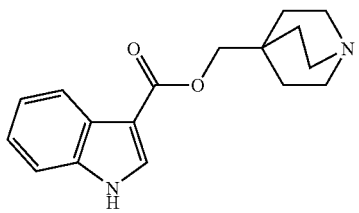

To a solution of 1H-indole-3-carbonyl chloride (45 mg, 0.25 mmol) in 3 mL of methylene chloride at 0° C. was added (quinuclidin-4-yl)methanol (36 mg, 0.25 mmol) in 2 mL of methylene chloride. The mixture was stirred at room temperature overnight. The solvent was evaporated and water (10 mL) was added. The water layer was basified to pH 12 using 10% aqueous potassium hydroxide and extracted three times with 25 mL each of ethyl acetate. The combined organic layers were dried over sodium sulfate and concentrated to yield 8 mg of desired product. $^1$HNMR: 12.02 (bs, 1H); 8.13 (d, 1H); 7.9 (m, 1H); 7.42 (m, 1H); 7.18 (m, 2H); 4.3 (bs, 2H); 3.03 (m, 6H); 1.75 (m, 6H). MS (m/e): 285.

Example 12

Quinuclidin-4-ylmethyl 5-chloro-1H-indole-3-carboxylate (6)

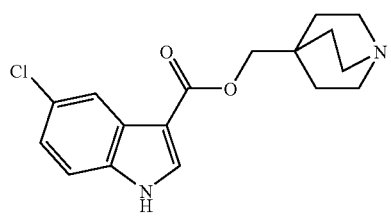

Quinuclidin-4-ylmethyl 5-chloro-1H-indole-3-carboxylate was prepared in a similar manner to (Quinuclidin-4-yl)methyl 1H-indole-3-carboxylate, substituting 5-chloro-1H-indole-3-carbonyl chloride as the electrophile.

Example 13

Quinuclidin-4-ylmethyl 2-methyl-1H-indole-3-carboxylate (9)

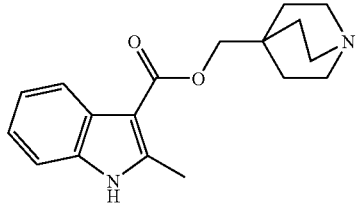

Quinuclidin-4-ylmethyl 2-methyl-1H-indole-3-carboxylate was prepared in a similar manner to (Quinuclidin-4-yl)methyl 1H-indole-3-carboxylate, substituting 2-methyl-1H-indole-3-carbonyl chloride as the electrophile.

Example 14

Quinuclidin-4-ylmethyl 1H-indazole-3-carboxylate (12)

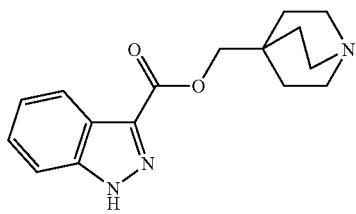

Quinuclidin-4-ylmethyl 1H-indazole-3-carboxylate was prepared in a similar manner to (Quinuclidin-4-yl)methyl 1H-indole-3-carboxylate, substituting 1H-indazole-3-carbonyl chloride as the electrophile.

Example 15

(3-Oxoquinuclidin-4-yl)methyl 1H-indole-3-carboxylate (11)

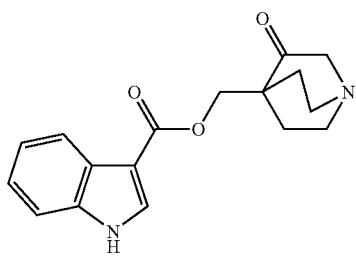

(3-oxoquinuclidin-4-yl)methyl 1H-indole-3-carboxylate was prepared in a similar manner to (Quinuclidin-4-yl)methyl 1H-indole-3-carboxylate, substituting 4-(Hydroxymethyl)quinuclidin-3-one as the nucleophile.

Example 16

N-((quinuclidin-4-yl)methyl)-1H-indole-3-carboxamide (1)

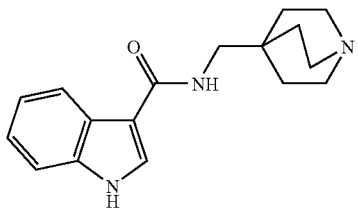

To a solution of 1H-indole-3-carbonyl chloride (112 mg, 0.625 mmol) in 3 mL of methylene chloride at 0° C. was added (quinuclidin-4-yl)methanamine (86 mg, 0.614 mmol) in 2 mL of methylene chloride. The mixture was stirred at room temperature overnight. The solvent was evaporated and water (20 mL) was added. The water layer was basified to pH 12 with 10% aqueous potassium hydroxide and extracted three times with 25 mL each of ethyl acetate. The combined organic layers were dried over sodium sulfate and concentrated to yield 26 mg of the desired product. $^1$HNMR: 11.6 (bs, 1H); 8.15 (m, 1H); 8.13 (bs, 1H); 7.65 (bs, 1H); 7.42 (d, 1H); 7.15 (m, 2H); 3.1 (m, 2H); 2.65 (m, 6H); 1.40 (m, 6H). MS (m/e): 284.

Example 17

N-((quinuclidin-4-yl)methyl)-1H-indazole-3-carboxamide (3)

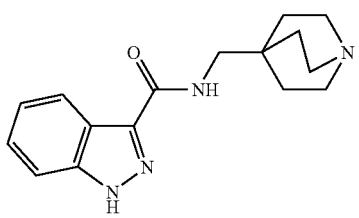

N-((quinuclidin-4-yl)methyl)-1H-indazole-3-carboxamide was prepared in a similar manner to N-((quinuclidin-4-yl)methyl)-1H-indole-3-carboxamide, substituting 1H-indazole-3-carbonyl chloride as the electrophile. $^1$HNMR: 13.6 (bs, 1H); 9.65 (bs, 1H); 8.45 (t, 1H); 8.15 (d, 1H); 7.62 (d, 1H); 7.41 (t, 1H); 7.2 (t, 1H); 3.28 (m, 2H); 3.21 (m, 6H); 1.70 (m, 6H). MS (m/e): 285.

Example 18

5-Fluoro-N-((quinuclidin-4-yl)methyl)-1H-indazole-3-carboxamide (4)

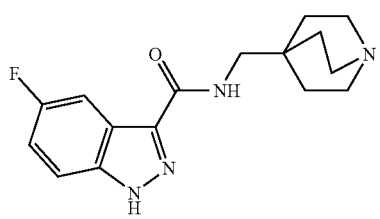

5-Fluoro-N-((quinuclidin-4-yl)methyl)-1H-indazole-3-carboxamide was prepared in a similar manner to N-((quinuclidin-4-yl)methyl)-1H-indole-3-carboxamide, substituting 5-fluoro-1H-indazole-3-carbonyl chloride as the electrophile. ¹HNMR: 10.6 (bs, 1H); 8.89 (t, 1H); 8.16 (dd, 1H); 7.9 (dd, 1H); 7.62 (m, 1H); 3.28 (m, 2H); 3.21 (m, 6H); 1.70 (m, 6H).

Example 19

N-(quinuclidin-4-ylmethyl)benzo[d]isothiazole-3-carboxamide (5)

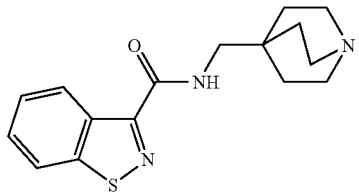

N-(quinuclidin-4-ylmethyl)benzo[d]isothiazole-3-carboxamide was prepared in a similar manner to N-((quinuclidin-4-yl)methyl)-1H-indole-3-carboxamide, substituting benzo[d]isothiazole-3-carbonyl chloride as the electrophile.

Example 20

Quinuclidin-4-ylmethyl 5-methoxy-1H-indole-3-carboxylate (13)

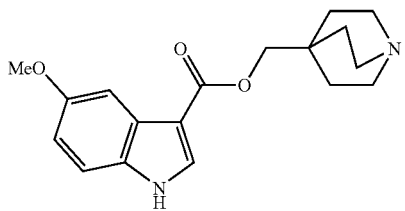

Quinuclidin-4-ylmethyl 5-methoxy-1H-indole-3-carboxylate was prepared starting from 5-methoxyindole-3-carboxylic acid (synthesized as described in J. Med. Chem. 49, 1125 (2006)) following the procedure of (Quinuclidin-4-yl)methyl 1H-indole-3-carboxylate. MS (m/e): 314.

Example 21

Quinuclidin-4-ylmethyl 6-methoxy-1H-indole-3-carboxylate (14)

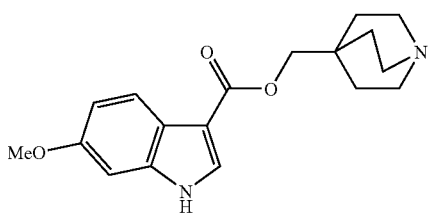

Quinuclidin-4-ylmethyl 6-methoxy-1H-indole-3-carboxylate was prepared starting from 6-methoxyindole-3-carboxylic acid (synthesized as described in J. Med. Chem. 51, 1849 (2008)) following the procedure of (Quinuclidin-4-yl)methyl 1H-indole-3-carboxylate. MS (m/e): 314.

Example 22

Quinuclidin-4-ylmethyl 5-(difluoromethoxy)-1H-indole-3-carboxylate (15)

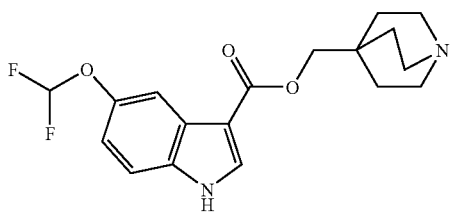

Quinuclidin-4-ylmethyl 5-(difluoromethoxy)-1H-indole-3-carboxylate was synthesized using the ester formation described for (Quinuclidin-4-yl)methyl 1H-indole-3-carboxylate. MS: (m/e) 350.

Example 23

Quinuclidin-4-ylmethyl 6-(difluoromethoxy)-1H-indole-3-carboxylate (16)

Quinuclidin-4-ylmethyl 6-(difluoromethoxy)-1H-indole-3-carboxylate was synthesized using the ester formation described for (Quinuclidin-4-yl)methyl 1H-indole-3-carboxylate. MS: (m/e) 350.

Example 24

Quinuclidin-4-ylmethyl 5-((trifluoromethoxy)methyl)-1H-indole-3-carboxylate (17)

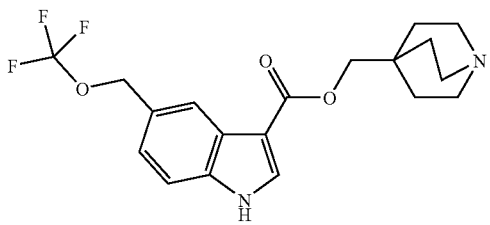

Quinuclidin-4-ylmethyl 5-((trifluoromethoxy)methyl)-1H-indole-3-carboxylate was synthesized using the ester formation described for (Quinuclidin-4-yl)methyl 1H-indole-3-carboxylate. MS: (m/e) 382.

Example 25

Quinuclidin-4-ylmethyl 5-isopropoxy-1H-indole-3-carboxylate (18)

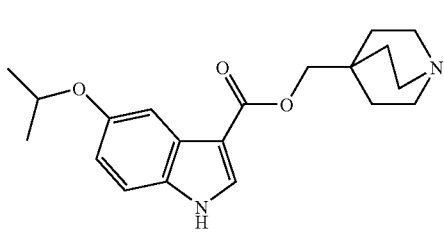

Quinuclidin-4-ylmethyl 5-isopropoxy-1H-indole-3-carboxylate was synthesized using the ester formation described for (Quinuclidin-4-yl)methyl 1H-indole-3-carboxylate. MS: (m/e) 342.

Example 26

Quinuclidin-4-ylmethyl 5-(cyclopropylmethoxy)-1H-indole-3-carboxylate (19)

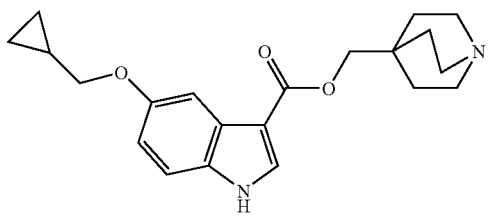

Quinuclidin-4-ylmethyl 5-(cyclopropylmethoxy)-1H-indole-3-carboxylate was synthesized using the ester formation described for (Quinuclidin-4-yl)methyl 1H-indole-3-carboxylate. MS: (m/e) 354.

Example 27

1-Azabicyclo[2.2.1]heptan-4-ylmethyl 1H-indole-3-carboxylate (20)

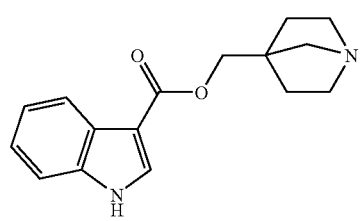

1-Azabicyclo[2.2.1]heptan-4-ylmethyl 1H-indole-3-carboxylate was synthesized using the procedure described for (Quinuclidin-4-yl)methyl 1H-indole-3-carboxylate using 1-Azabicyclo[2.2.1]heptan-4-ylmethanol. MS: (m/e) 270.

Example 28

1-Azabicyclo[2.2.1]heptan-4-ylmethyl 5-fluoro-1H-indole-3-carboxylate (21)

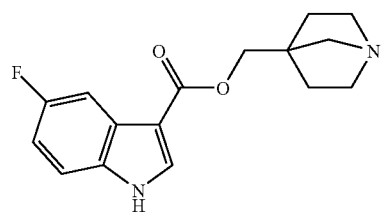

1-Azabicyclo[2.2.1]heptan-4-ylmethyl 5-fluoro-1H-indole-3-carboxylate was synthesized using the procedure described for (Quinuclidin-4-yl)methyl 1H-indole-3-carboxylate using 1-Azabicyclo[2.2.1]heptan-4-ylmethanol. MS: (m/e) 288.

Example 29

1-Azabicyclo[2.2.1]heptan-4-ylmethyl 5-chloro-1H-indole-3-carboxylate (22)

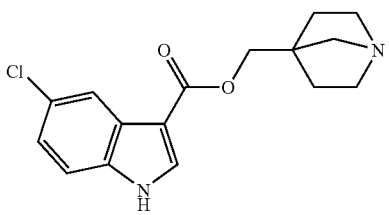

1-Azabicyclo[2.2.1]heptan-4-ylmethyl 5-chloro-1H-indole-3-carboxylate was synthesized using the procedure described for (Quinuclidin-4-yl)methyl 1H-indole-3-carboxylate using 1-Azabicyclo[2.2.1]heptan-4-ylmethanol. MS: (m/e) 305.

Example 30

1-Azabicyclo[2.2.1]heptan-4-ylmethyl 5-methoxy-1H-indole-3-carboxylate (23)

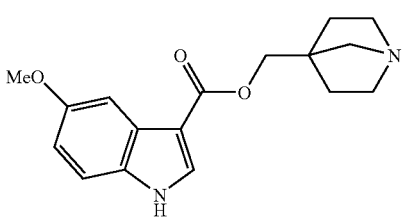

1-Azabicyclo[2.2.1]heptan-4-ylmethyl 5-methoxy-1H-indole-3-carboxylate was synthesized using the procedure described for (Quinuclidin-4-yl)methyl 1H-indole-3-carboxylate using 1-Azabicyclo[2.2.1]heptan-4-ylmethanol. MS: (m/e) 300.

Example 31

1-Azabicyclo[2.2.1]heptan-4-ylmethyl 5-(difluoromethoxy)-1H-indole-3-carboxylate (24)

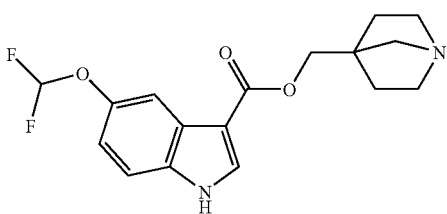

1-Azabicyclo[2.2.1]heptan-4-ylmethyl 5-(difluoromethoxy)-1H-indole-3-carboxylate was synthesized using the procedure described for (Quinuclidin-4-yl)methyl 1H-indole-3-carboxylate using 1-Azabicyclo[2.2.1]heptan-4-ylmethanol. MS: (m/e) 336.

Example 32

1-Azabicyclo[2.2.1]heptan-4-ylmethyl 6-methoxy-1H-indole-3-carboxylate (25)

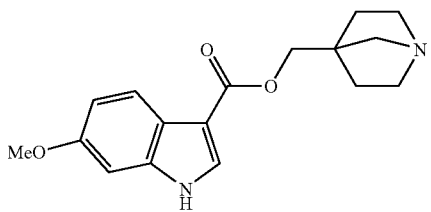

1-Azabicyclo[2.2.1]heptan-4-ylmethyl 6-methoxy-1H-indole-3-carboxylate was synthesized using the procedure described for (Quinuclidin-4-yl)methyl 1H-indole-3-carboxylate using 1-Azabicyclo[2.2.1]heptan-4-ylmethanol. MS: (m/e) 300.

Example 33

1-Azabicyclo[2.2.1]heptan-4-ylmethyl 6-(difluoromethoxy)-1H-indole-3-carboxylate (26)

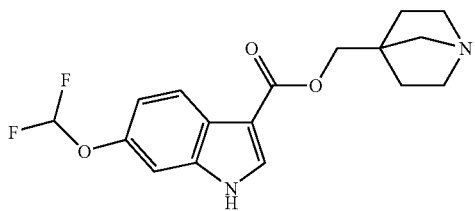

1-Azabicyclo[2.2.1]heptan-4-ylmethyl 6-(difluoromethoxy)-1H-indole-3-carboxylate was synthesized using the procedure described for (Quinuclidin-4-yl)methyl 1H-indole-3-carboxylate using 1-Azabicyclo[2.2.1]heptan-4-ylmethanol. MS: (m/e) 336.

Example 34

Rat Brain Nicotinic Receptor Radioligand Binding Assays

After decapitation, washed whole rat brain membranes (200 µg of protein) were prepared according to the method used by Marks and Collins, Mol. Pharmacol. 22, 554 (1982). Before use, the washed membranes were resuspended in 500 µL receptor binding assay saline (pH 7.4) consisting of 120 mM NaCl, 5 mM KCl, 2 mM $CaCl_2$, 1 mM $MgCl_2$ and 50 mM Tris-HCl.

[$^3$H]Cytisine (35 Ci/mmol)-binding displacement experiments (a measure of binding affinity at the rat α4β2 receptor subtype) were performed essentially according to Flores et al., Mol. Pharmacol. 41, 31 (1992), except that the incubation time was increased to 4 h at 0 to 4° C. to ensure equilibrium during the competition binding assay.

Binding of $^{125}$I-BTX (136 Ci/mmol) (a measure of binding affinity at the rat α7 receptor subtype) was performed at 37° C. for 3 h; the saline solution mentioned above also contained 2 mg/mL bovine serum albumin.

Nonspecific binding of each radioligand was measured in the presence of 1.0 mM nicotine (Marks and Collins, 1982). After incubation, membranes with bound radioligand were collected on Whatman GF/C glass fiber filters presoaked for 45 min in 0.5% polyethylenimine and washed three times with 3.0 mL of ice-cold buffer by vacuum filtration on a harvester (Brandel, Gaithersburg, Md.).

Bound [$^3$H]cytisine was measured in a liquid scintillation counter, whereas [$^{125}$I]BTX was measured with use of a Biogamma counter (both from Beckman Coulter). Binding data were analyzed using Prism software (GraphPad Software Inc., San Diego, Calif.). All $K_i$ values were calculated from the Cheng-Prusoff equation, using a $K_d$ value for each radioligand that had been experimentally determined under conditions identical with those of the displacement experiments.

In the [$^{125}$I] BTX assay (a measure of binding affinity at the rat α7 receptor subtype), agents of the invention exhibit $K_i$ values from about 20 nM to about 1 µM. In the [$^3$H]cytisine assay (a measure of binding affinity at the rat α4β2 receptor subtype), agents of the invention exhibit $K_i$ values from about 500 nM to about 50 µM, demonstrating selectivity of agents of the invention for the α7 nACh receptor subtype.

Example 35

Novel Object Recognition Task (NORT)

Procedure—The object recognition task experiments were similar to those described by Ennaceur and Delacour (Behav. Brain Res. 31, 47 (1988)) in young rats. The experiments were carried out during a 3 day period in three separate sessions. During the first session (context habituation), the subjects were allowed 20 min to become acquainted with the apparatus. On day 2 the rats were administered vehicle or test compound either i.v. or p.o. One hour after administration of vehicle or test compound the rats were subjected to an acquisition phase during which they were exposed to a pair of identical objects for 3 min. The time spent with the familiar object was recorded. Animals were then returned to their home cages. On day 3 the rats were treated with vehicle or test compound either i.v. or p.o. The rats were then subjected to a choice trial for a period of 3 minutes. In this instance the rats were allowed to explore the arena in which a copy of the familiar object is used along with a novel object. The time spent with the novel as well as the familiar object were each recorded.

Data Analysis—The time periods spent with the novel and the familiar object were compared using a paired t-test. Discriminative indices were analyzed by ANOVA followed by post-hoc Dunnet's test. Several test compounds showed cognition-enhancing properties in this test when dosed within a range of 0.1 to 50 mg/kg.

What is claimed is:

1. A compound having the formula:

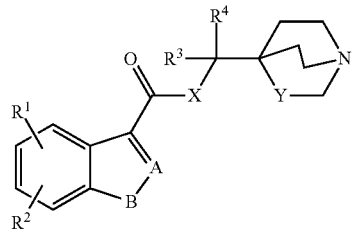

wherein

A is —N—; —CH—; or —C($C_1$-$C_6$ alkyl)-, optionally substituted with one or more groups selected from hydroxyl and halo;

B is —NH—; —N($C_1$-$C_6$ alkyl)-, optionally substituted with one or more groups selected from hydroxyl and halo; —O—; or —S—;

X is —O—; —NH—; —N($C_1$-$C_6$ alkyl)-, optionally substituted with one or more groups selected from hydroxyl and halo; —CH$_2$—; or a bond;

Y is a bond, —CH$_2$—, —(CH$_2$)$_2$—, —OCH$_2$—, —C(O)—, —CH(OR$^7$)—, —C(OR$^7$)$_2$—,

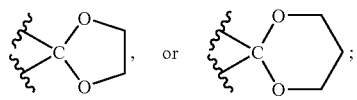

$R^7$ is independently —$C_1$-$C_6$ alkyl, optionally substituted with one or more groups selected from hydroxyl and halo;

$R^1$ and $R^2$ are each independently —H; —OH; —$C_1$-$C_6$ alkoxy, optionally substituted with one or more groups selected from hydroxyl and halo; —$C_1$-$C_6$ alkyl, optionally substituted with one or more groups selected from hydroxyl and halo; —$C_1$-$C_6$ alkyl-($C_1$-$C_6$ alkoxy), optionally substituted with one or more groups selected from hydroxyl and halo; halo; —NO$_2$; —CN; —C(O)N(R$_5$)R$_6$; —S(O)$_2$R$_5$; —S(O)$_2$N(R$_5$)R$_6$; or wherein $R^1$ and $R^2$ are at adjacent carbons and together substituted with —O—CH$_2$—O— to form a ring; and $R^3$, $R^4$, $R^5$, and $R^6$ are each independently —H or —$C_1$-$C_6$ alkyl, optionally substituted with one or more groups selected from hydroxyl and halo;

with the proviso that when A is —N— or —CH—, B is —NH— or —N($C_1$-$C_3$ alkyl)-, X is —O—, Y is —CH$_2$—, $R^3$ and $R^4$ are —H, and one of $R^1$ and $R^2$ is —H, then the other of $R^1$ and $R^2$ is not 7-alkoxy; or a pharmaceutically acceptable salt thereof.

2. The compound of claim 1, wherein:

A is —N—; —CH—; or —C($C_1$-$C_3$ alkyl)-;

B is —NH—; —N($C_1$-$C_3$ alkyl)-; —O—; or —S—;

X is —O—; —NH—; —N($C_1$-$C_3$ alkyl)-; —CH$_2$—; or a bond;

Y is a bond, —CH$_2$—, —(CH$_2$)$_2$—, —OCH$_2$—, —C(O)—, —CH(OR$^7$)—, —C(OR$^7$)$_2$—,

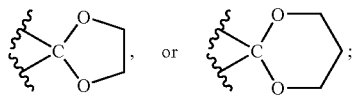

$R^7$ is —$C_1$-$C_3$ alkyl;

$R^1$ and $R^2$ are each independently —H; —OH; —$C_1$-$C_6$ alkoxy, optionally substituted with hydroxyl; $C_1$-$C_6$ alkyl, optionally substituted with hydroxyl; halo; —NO$_2$; —CN; —C(O)N(R$_5$)R$_6$; —S(O)$_2$R$_5$; —S(O)$_2$N(R$_5$)R$_6$, —OCF$_3$, —OCHF$_2$, —OCF$_3$; or wherein $R^1$ and $R^2$ are at adjacent carbons and together substituted with —O—CH$_2$—O— to form a ring; and where $R^3$, $R^4$, $R^5$, and $R^6$ are each independently —H or —$C_1$-$C_3$ alkyl;

or a pharmaceutically acceptable salt thereof.

3. The compound of claim 1, wherein:

A is —N—; —CH—; or —C($C_1$-$C_6$ alkyl)-, optionally substituted with one or more groups selected from hydroxyl and halo;

B is —NH—; —N($C_1$-$C_6$ alkyl)-, optionally substituted with one or more groups selected from hydroxyl and halo; —O—; or —S—;

X is O, CH$_2$, or a bond;

Y is a bond, —CH$_2$—, —(CH$_2$)$_2$—, —OCH$_2$—, —C(O)—, —CH(OR$^7$)—, —C(OR$^7$)$_2$—,

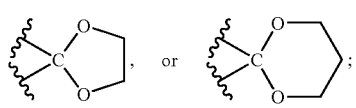

$R^7$ is —$C_1$-$C_6$ alkyl, optionally substituted with one or more groups selected from hydroxyl and halo;

$R^1$ and $R^2$ are each independently —H; —OH; —$C_1$-$C_6$ alkoxy, optionally substituted with one or more groups selected from hydroxyl and halo; —$C_1$-$C_6$ alkyl, optionally substituted with one or more groups selected from hydroxyl and halo; —$C_1$-$C_6$ alkyl-($C_1$-$C_6$ alkoxy), optionally substituted with one or more groups selected from hydroxyl and halo; halo; —NO$_2$; —CN; —C(O)N(R$_5$)R$_6$; —S(O)$_2$R$_5$; —S(O)$_2$N(R$_5$)R$_6$; or wherein $R^1$ and $R^2$ are at adjacent carbons and together substituted with —O—CH$_2$—O— to form a ring; and $R^3$, $R^4$, $R^5$, and $R^6$ are each independently —H or —$C_1$-$C_6$ alkyl, optionally substituted with one or more groups selected from hydroxyl and halo;

or a pharmaceutically acceptable salt thereof.

4. The compound of claim 1 wherein:
A is —N—; —CH—; or —C(C$_1$-C$_3$ alkyl)-;
B is —NH—; —N(C$_1$-C$_3$ alkyl)-; —O—; or —S—;
X is —O—; —CH$_2$—; or a bond;
Y is a bond, —CH$_2$—, —(CH$_2$)$_2$—, —OCH$_2$—, —C(O)—, —CH(OR$^7$)—, —C(OR$^7$)$_2$—,

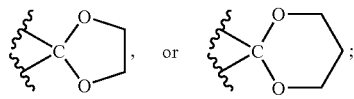

R$^7$ is —C$_1$-C$_3$ alkyl;
R$^1$ and R$^2$ are each independently —H; —OH; —C$_1$-C$_6$ alkoxy, optionally substituted with hydroxyl; C$_1$-C$_6$ alkyl, optionally substituted with hydroxyl; halo; —NO$_2$; —CN; —C(O)N(R$_5$)R$_6$; —S(O)$_2$R$_5$; —S(O)$_2$N(R$_5$)R$_6$, —OCF$_3$, —OCHF$_2$, —OCF$_3$; or wherein R$^1$ and R$^2$ are at adjacent carbons and together substituted with —O—CH$_2$—O— to form a ring; and
where R$^3$, R$^4$, R$^5$, and R$^6$ are each independently —H or —C$_1$-C$_3$ alkyl;
or a pharmaceutically acceptable salt thereof.

5. The compound of claim 1, wherein A is —N—, —CH—, or —C(CH$_3$)—; or a pharmaceutically acceptable salt thereof.

6. The compound of claim 5, wherein A is —N—; or a pharmaceutically acceptable salt thereof.

7. The compound of claim 5, wherein A is —CH—; or a pharmaceutically acceptable salt thereof.

8. The compound of claim 1, wherein B is —NH— or —S—; or a pharmaceutically acceptable salt thereof.

9. The compound of claim 8, wherein B is —NH—; or a pharmaceutically acceptable salt thereof.

10. The compound of claim 8, wherein B is —S—; or a pharmaceutically acceptable salt thereof.

11. The compound of claim 1, wherein X is —O— or —NH—; or a pharmaceutically acceptable salt thereof.

12. The compound of claim 11, wherein X is —O—; or a pharmaceutically acceptable salt thereof.

13. The compound of claim 11, wherein X is —NH—; or a pharmaceutically acceptable salt thereof.

14. The compound of claim 1, wherein Y is —CH$_2$—, —C(O)—, or a bond; or a pharmaceutically acceptable salt thereof.

15. The compound of claim 14, wherein Y is —CH$_2$—; or a pharmaceutically acceptable salt thereof.

16. The compound of claim 14, wherein Y is a bond; or a pharmaceutically acceptable salt thereof.

17. The compound of claim 1, wherein R$^1$ and R$^2$ are each independently —H; —OH; —C$_1$-C$_6$ alkyl, optionally substituted with hydroxyl or halo; —C$_1$-C$_6$ alkoxy; halo; —NO$_2$; —CN; —C(O)N(R$_5$)R$_6$; —S(O)$_2$R$_5$; —S(O)$_2$N(R$_5$)R$_6$; —OCH$_2$F, —OCHF$_2$; —OCF$_3$; or wherein R$^1$ and R$^2$ are together substituted with —O—CH$_2$—O— to form a ring; or a pharmaceutically acceptable salt thereof.

18. The compound of claim 1, wherein R$^1$ and R$^2$ are each independently —H; —NO$_2$, —CN, —OH, —C$_1$-C$_3$ alkyl, optionally substituted with halo; halo; —C$_1$-C$_3$ alkoxy; —C(O)NH$_2$; —S(O)$_2$NHMe; —SO$_2$CH$_3$; —OCH$_2$F; —OCHF$_2$; —OCF$_3$; or a pharmaceutically acceptable salt thereof.

19. The compound of claim 1, wherein R$^1$ and R$^2$ are each independently —H, halo or —OCH$_3$; or a pharmaceutically acceptable salt thereof.

20. The compound of claim 1, wherein at least one of R$^1$ and R$^2$ is —H; or a pharmaceutically acceptable salt thereof.

21. The compound of claim 1, wherein one of R$^1$ or R$^2$ is located at the 5-position and is other than —H; or a pharmaceutically acceptable salt thereof.

22. The compound of claim 1, wherein both R$^1$ and R$^2$ are —H; or a pharmaceutically acceptable salt thereof.

23. The compound of claim 1, wherein both R$^3$ and R$^4$ are —H; or a pharmaceutically acceptable salt thereof.

24. The compound of claim 1, wherein A is —N—, —CH—, or —C(C$_1$-C$_3$ alkyl)-; B is —NH—, —O—, or —S—; X is —O— or —NH—; Y is a bond, —CH$_2$—, or —C(O)—; R$^1$ and R$^2$ are each independently —H; —OH; —C$_1$-C$_6$ alkoxy, optionally substituted with halo; —C$_1$-C$_6$ alkyl, optionally substituted with halo; halo; —CN; or —C(O)N(R$_5$)R$_6$; and where R$^3$, R$^4$, R$^5$, and R$^6$ are each —H; or a pharmaceutically acceptable salt thereof.

25. The compound of claim 24, wherein A is —N—, —CH—, or —C(CH$_3$)—; B is —NH—, —O—, or —S—; X is —O—; Y is —CH$_2$— or a bond; R$^1$ and R$^2$ are each independently —H; halo; —CN; —C(O)N(R$_5$)R$_6$, or —OCH$_3$; and where R$^3$, R$^4$, R$^5$, and R$^6$ are each —H; or a pharmaceutically acceptable salt thereof.

26. The compound of claim 24, wherein A is —N—, —CH—, or —C(CH$_3$)—; B is —NH—, —O—, or —S—; X is —NH—; Y is —CH$_2$— or a bond; R$^1$ and R$^2$ are each independently —H; halo; —CN; —C(O)N(R$_5$)R$_6$, or —OCH$_3$ and where R$^3$, R$^4$, R$^5$, and R$^6$ are each —H; or a pharmaceutically acceptable salt thereof.

27. The compound of claim 1, wherein the compound is selected from the group consisting of:
N-(quinuclidin-4-ylmethyl)-1H-indole-3-carboxamide,
Quinuclidin-4-ylmethyl 1H-indole-3-carboxylate,
N-(quinuclidin-4-ylmethyl)-1H-indazole-3-carboxamide,
5-Fluoro-N-(quinuclidin-4-ylmethyl)-1H-indazole-3-carboxamide,
N-(quinuclidin-4-ylmethyl)benzo[d]isothiazole-3-carboxamide,
Quinuclidin-4-ylmethyl 5-chloro-1H-indole-3-carboxylate,
Quinuclidin-4-ylmethyl 5-cyano-1H-indole-3-carboxylate,
Quinuclidin-4-ylmethyl 5-carbamoyl-1H-indole-3-carboxylate,
Quinuclidin-4-ylmethyl 2-methyl-1H-indole-3-carboxylate,
Quinuclidin-4-ylmethyl 5-methoxy-2-methyl-1H-indole-3-carboxylate,
(3-Oxoquinuclidin-4-yl)methyl 1H-indole-3-carboxylate,
Quinuclidin-4-ylmethyl 1H-indazole-3-carboxylate,
Quinuclidin-4-ylmethyl 5-methoxy-1H-indole-3-carboxylate,
Quinuclidin-4-ylmethyl 6-methoxy-1H-indole-3-carboxylate,
Quinuclidin-4-ylmethyl 5-(difluoromethoxy)-1H-indole-3-carboxylate,
Quinuclidin-4-ylmethyl 6-(difluoromethoxy)-1H-indole-3-carboxylate,
Quinuclidin-4-ylmethyl 5-((trifluoromethoxy)methyl)-1H-indole-3-carboxylate,
Quinuclidin-4-ylmethyl 5-isopropoxy-1H-indole-3-carboxylate,
Quinuclidin-4-ylmethyl 5-(cyclopropylmethoxy)-1H-indole-3-carboxylate,
1-azabicyclo[2.2.1]heptan-4-ylmethyl 1H-indole-3-carboxylate, 1-azabicyclo[2.2.1]heptan-4-ylmethyl 5-fluoro-1H-indole-3-carboxylate, 1-azabicyclo[2.2.1]heptan-4-ylmethyl 5-chloro-1H-indole-3-carboxylate, 1-azabicyclo[2.2.1]heptan-4-ylmethyl 5-methoxy-1H-indole-3-carboxylate, 1-azabicyclo[2.2.1]heptan-4-ylmethyl 5-(difluoromethoxy)-1H-indole-3-carboxylate, 1-azabicyclo[2.2.1]heptan-4-ylmethyl 6-methoxy-1H-indole-3-carboxylate, and 1-azabicyclo[2.2.1]heptan-4-ylmethyl 6-(difluoromethoxy)-1H-indole-3-carboxylate;

or a pharmaceutically acceptable salt thereof.

28. The compound of claim 1, wherein the compound is quinuclidin-4-ylmethyl 1H-indole-3-carboxylate; or pharmaceutically acceptable salt thereof.

29. The compound of claim 1, wherein the compound is present in substantially pure form.

30. A formulation comprising an effective amount of a compound of claim 1, or a pharmaceutically acceptable salt thereof; and a pharmaceutically acceptable carrier.

31. A method for the treatment of a condition selected from the group consisting of schizophrenia, pain, general anxiety disorder, cognitive deficits associated with schizophrenia, and cognitive deficits associated with psychosis, comprising the step of:
(a) administering to an individual in need thereof a therapeutically effective amount of a compound of claim 1, or a pharmaceutically acceptable salt thereof.

32. The method of claim 31 further comprising the step:
(b) administering to the individual a pharmaceutical agent, additional treatment modality, or combination thereof.

33. The method of claim 32, wherein the pharmaceutical agent is selected from the group consisting of an acetylcholinesterase inhibitor, an antipsychotic agent, and an NMDA antagonist.

34. The method of claim 33, wherein the pharmaceutical agent is an acetylcholinesterase inhibitor selected from the group consisting of donepezil, rivastigmine, and galantamine.

35. The method of claim 33, wherein the pharmaceutical agent is an antipsychotic agent selected from the group consisting of aripiprazole, ziprasidone, zotepine, risperidone, quetiapine, clozapine, thiothixene, thioridazine, loxapine, haloperidol, fluphenazine and chlorpromazine.

36. The method of claim 33, wherein the pharmaceutical agent is the NMDA antagonist memantine.

37. A kit for the treatment in an individual of a condition selected from the group consisting of schizophrenia, pain, general anxiety disorder, cognitive deficits associated with schizophrenia, and cognitive deficits associated with psychosis, comprising:
(a) the compound of claim 1, or a pharmaceutically acceptable salt thereof; and
(b) packaging.

38. The method of claim 31, wherein said condition is schizophrenia or cognitive deficits associated with schizophrenia.

39. The method of claim 31, wherein said condition is cognitive deficits associated with psychosis.

40. The method of claim 31, wherein said condition is pain.

41. The method of claim 31, wherein said condition general anxiety disorder.

* * * * *